United States Patent
Olsson et al.

(10) Patent No.: US 10,001,425 B1
(45) Date of Patent: Jun. 19, 2018

(54) PORTABLE CAMERA CONTROLLER PLATFORM FOR USE WITH PIPE INSPECTION SYSTEM

(75) Inventors: Mark S. Olsson, La Jolla, CA (US); Alexander L. Warren, San Diego, CA (US); David A. Cox, San Diego, CA (US); Wesley Ice, San Diego, CA (US); Jesse O. Casares, El Cajon, CA (US); Stephanie M. Bench, Carlsbad, CA (US); Michael E. Turgeon, San Diego, CA (US); Michael J. Martin, San Diego, CA (US); Paul G. Stuart, Lemon Grove, CA (US)

(73) Assignee: SEESCAN, INC., San Diego, CA (US)

( * ) Notice: Subject to any disclaimer, the term of this patent is extended or adjusted under 35 U.S.C. 154(b) by 1250 days.

(21) Appl. No.: 13/346,668

(22) Filed: Jan. 9, 2012

Related U.S. Application Data

(60) Provisional application No. 61/430,932, filed on Jan. 7, 2011.

(51) Int. Cl.
*H04N 7/18* (2006.01)
*G01M 3/00* (2006.01)

(52) U.S. Cl.
CPC .................................... *G01M 3/005* (2013.01)

(58) Field of Classification Search
None
See application file for complete search history.

(56) References Cited

U.S. PATENT DOCUMENTS

| 7,032,872 | B2 | 4/2006 | Sullivan | |
|---|---|---|---|---|
| 8,514,278 | B2 * | 8/2013 | Karpen et al. | 348/80 |
| 2003/0057340 | A1 | 3/2003 | Mann et al. | |
| 2007/0034753 | A1 | 2/2007 | Lee | |
| 2007/0120034 | A1 | 5/2007 | Sparling | |
| 2008/0023283 | A1 | 1/2008 | Sutker et al. | |
| 2011/0108654 | A1 * | 5/2011 | Babb et al. | 242/400 |
| 2012/0069172 | A1 * | 3/2012 | Hudritsch | 348/84 |

FOREIGN PATENT DOCUMENTS

WO    WO 2010057244 A1 *   5/2010

\* cited by examiner

*Primary Examiner* — James M Anderson, II
(74) *Attorney, Agent, or Firm* — Steven C. Tietsworth, Esq.

(57) ABSTRACT

A camera controller platform for use with a pipe inspection system is disclosed. The platform is configured for the rapid mounting and connection of an electronic computing device such as a laptop computer for providing display and/or virtual control interface functions in conjunction with an electronics module. An additional user interface, which may include a manual user interface device, may be coupled to the electronics module. Alternatively, a plurality of virtual controls may be supported by a software application on the electronic computing device, which may be connected to the camera controller platform by a USB or other interface bus.

18 Claims, 21 Drawing Sheets

DataLink Payload Data Interpretation

| Type | | Byte | Value | Meaning |
|---|---|---|---|---|
| Count Information (cm) | 246 | 1 | 0x80 | Count Message ID |
| | | 2 - 5 | 0 - xxx | Count (cm) |
| | | 6 | 0x0 - 0xFF | Checksum |
| Raw Count Information | 248 | 1 | 0x81 | Raw Count Message ID |
| | | 2 - 5 | 0 - xxx | Power On Count |
| | | 6 - 9 | 0 - xxx | Temp Zero Count |
| | | 10 - 13 | 0 - xxx | Current Count |
| | | 14 | 0x0 - 0xFF | Checksum |
| Measurement Origin | 250 | 1 | 0x82 | Measurement Origin Message ID |
| | | 2 | 0 or 1 | Power On, Absolute or Relative Count State |
| | | 3 | 0x0 - 0xFF | Checksum |
| Odometer Information | 252 | 1 | 0x83 | Odometer Message ID |
| | | 2 - 5 | 0 - xxx | Odometer Count (cm) |
| | | 6 | 0x0 - 0xFF | Checksum |

FIG. 10A

DataLink Payload Data Interpretation

| Type | Byte | Value | Meaning |
|---|---|---|---|
| Reel Information | 1 | 0x84 | Reel Info ID |
| (254) | 2 - 4 | 0 - xxx | Cable Length (ft) |
| | 5 | 0x00 -- 0x02 | Reel Type |
| | 6 | 0x00 -- 0x02 | Cable Type |
| | 7 | 0x0 -- 0xFF | Checksum |
| Raw Total Count Information | 1 | 0x85 | Raw Count Message ID |
| (256) | 2 - 5 | 0 - xxx | Total Sum Raw 32-Bit Count |
| | 6 | 0x0 - 0xFF | Checksum |
| Software Version | 1 | 0xF0 | Software Version Message ID |
| (258) | 2 - 5 | 0 - xxx | Software Version |
| | 6 | 0x0 - 0xFF | Checksum |

FIG. 10B

PORTABLE CAMERA CONTROLLER PLATFORM FOR USE WITH PIPE INSPECTION SYSTEM

CROSS-REFERENCE TO RELATED APPLICATIONS

This applications claims priority under 35 U.S.C. § 119(e) to U.S. Provisional Patent Application Ser. No. 61/430,932, entitled PORTABLE CAMERA CONTROLLER PLATFORM FOR USE WITH PIPE INSPECTION SYSTEM, filed on Jan. 7, 2011, the content of which is incorporated by reference herein in its entirety for all purposes.

FIELD

This disclosure relates generally to portable pipe inspection systems and related accessories and apparatus. More specifically, but not exclusively, the disclosure relates to camera controller platform for use with a pipe inspection system.

BACKGROUND

Pipes are often prone to obstructions through a variety of mechanical, structural, and/or environmental factors, such as for example, invasion by tree roots and/or other vegetation, build-up and corrosion, as well as other blockages. Various devices and methods for visualizing the interior of a pipe are known in the art. For example, current pipe inspection systems typically include a camera head coupled to the end of a cable to inspect the interior of pipes, conduits, and other voids, and the images collected are elucidated on a display device. However, current systems are bulky and difficult to transport to a remote location.

Accordingly, there is a need in the art to address the above-described, as well as other problems.

SUMMARY

The present disclosure relates generally to apparatus, systems, and methods for pipe inspection. More specifically, but not exclusively, the disclosure relates to a portable camera controller platform and associated pipe inspection system.

For example, in one aspect, the disclosure relates to a pipe inspection system including a portable camera controller platform. The pipe inspection system may include, for example, a camera head coupled to the end of a push-cable, and a cable storage drum. The pipe inspection system may further include, for example, a camera controller platform, which may include a base assembly or base structure configured for mounting to a support element of the cable storage drum. The pipe inspection system may further include, for example, an electronic computing device, such as a computer or display device, which may be mounted to the platform base. The camera controller platform may include, for example, a user interface device or element to provide data exchange between the camera head and display device. The interface may include, for example, a front panel configured with a control keypad, touchscreen, or other user interface element, such as a magnetic user interface device.

In another aspect, the disclosure relates to a camera controller platform system. The camera controller platform system may include, for example, a fastener for securing an electronic computing device, such as a laptop computer or other display device, onto the base platform. The device may be secured using a capstan. The camera controller platform system may further include, for example, at least one rotatable and/or extendable platform extension wing. The camera controller platform system may further include, for example, a processing element including a processor and a USB bus connected to the processor. The camera controller platform system may further include, for example, a system cable plug or connector for connecting the platform to an interface circuit coupled to the cable storage drum and a camera head, using a system connector cable. The camera controller platform system may further include, for example, a control pad on a user interface for providing control commands to the camera head. Programming may be stored at least partially in firmware in the platform, enabling the control pad to interact with the pipe inspection system and laptop computer or other electronic computing system.

In another aspect, the disclosure relates to a portable camera controller platform. The platform may include, for example, a base assembly configured to mechanically couple the platform to a pipe inspection system including a cable reel drum assembly and a camera head. The base assembly may be configured to be fully or partially integrated with the cable reel drum assembly. The platform may further include a user interface panel disposed on or in the base assembly. The platform may further include an electronics module coupled to the user interface panel. The electronics module may include one or more processing elements configured to receive control input signals from the user interface panel and provide control data the pipe inspection system. The processing element(s) may be further configured to receive one or more pipe inspection output signals from the pipe inspection system and provide data corresponding to the pipe inspection output signals to an electronic computing system.

In another aspect, the disclosure relates to a pipe inspection system. The pipe inspection system may include, for example, a cable reel drum assembly, a push-cable coupled to the cable-reel drum assembly, a camera head coupled to a distal end of the push-cable, and an interface circuit configured to electronically couple the camera head to a first end of a system cable. The pipe inspection system may further include a camera controller platform. The platform may include a base assembly configured to mechanically couple the platform to a pipe inspection system including a cable reel drum assembly and a camera head, a user interface panel disposed on or in the base assembly, and an electronics module coupled to the user interface panel. The electronics module may include one or more processing elements configured to receive control input signals from the user interface panel and provide control data the pipe inspection system, and receive one or more pipe inspection output signals from the pipe inspection system and provide data corresponding to the pipe inspection output signals to an electronic computing system. The system may further include a a system connector coupled to the electronics module and to a second end of the system cable. The platform may be incorporated at least in part into the cable reel drum assembly.

In another aspect, the disclosure relates to a camera controller platform. The platform may include, for example, a base assembly, a user interface panel disposed on or in the base assembly, and an electronics module coupled to the user interface panel. The electronics module may include one or more processing elements. The processing elements may be configured to receive control input signals from the user interface panel and provide control data to a pipe inspection system, and receive one or more pipe inspection output signals from the pipe inspection system and provide data corresponding to the pipe inspection output signals to an electronic computing system.

In another aspect, the disclosure relates to a pipe inspection system. The pipe inspection system may include, for example, a cable reel drum assembly, a push-cable coupled to the cable-reel drum assembly, a camera head coupled to a distal end of the push-cable, and an interface circuit configured to electronically couple the camera head to a first end of a system cable. The pipe inspection system may further include a camera controller platform. The platform may include a base assembly, a user interface panel disposed on or in the base assembly, an electronics module coupled to the user interface panel. The electronics module may include one or more processing elements configured to receive control input signals from the user interface panel and provide control data the pipe inspection system, and receive one or more pipe inspection output signals from the pipe inspection system and provide data corresponding to the pipe inspection output signals to an electronic computing system. The pipe inspection system may further include a system connector coupled to the electronics module and to a second end of the system cable.

In another aspect, the disclosure relates to methods and processing for implementing the camera system functionality as described above, in whole or in part.

In another aspect, the disclosure relates to means for implementing the above-described methods and/or system or device functions, in whole or in part.

In another aspect, the disclosure relates to computer-readable media including instructions for causing a computer or processing element to implement the camera system functionality described above, in whole or in part.

Various additional aspects, features, and functionality are further described below in conjunction with the appended Drawings.

BRIEF DESCRIPTION OF THE DRAWINGS

The present disclosure may be more fully appreciated in connection with the following detailed description taken in conjunction with the accompanying drawings, wherein:

FIGS. 10A and 10B are a data table illustrating data links of the pipe inspection system;

DETAILED DESCRIPTION

Terminology

Figure 1:
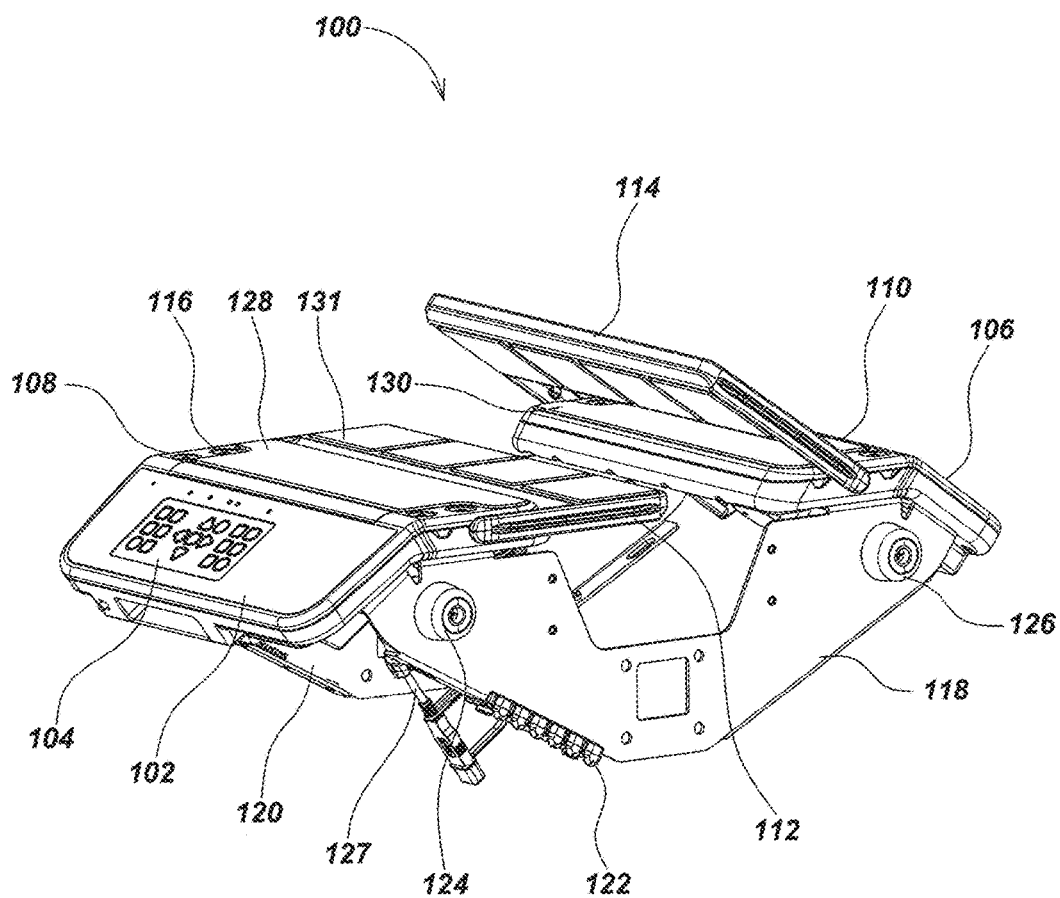
FIG. 1 is an isometric view of an embodiment of a portable camera controller platform.

The term "electronic computing device" as used herein refers to an electronic device or system including data input, processing, and display functionality and optionally other functionality such as receiving user input and control actions, providing data storage, communications interfaces to external devices or systems, as well as providing other computer-related functions. Examples of electronic computing devices include, but are not limited to, personal computer devices such as laptop or notebook computers, tablet devices, such as Android or Ipad devices, smart phones, and similar devices. In some embodiments, electronic computing devices may also include other devices such as monitoring and control system devices, instrumentation devices, or other similar or equivalent computer or processor-based systems or devices that include processing and display functionality.

The term "processing element" as used herein refers to an electronic circuit for performing signal and data processing and related functions. A processing element may be implemented or processing functions performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, special purpose processing and/or state machine or other programmable device. A processor may also be implemented as a combination of computing devices, e.g., a combination of a DSP and a microprocessor, a plurality of microprocessors, one or more microprocessors in conjunction with a DSP core, or any other such configuration. A processing element may furthering include or be coupled to one or more memory elements, for storing instructions, data, and/or other information in a digital storage format, as well as interface and signal conditioning element, Input/Output (I/O) elements and the like.

The term "interface bus" as used herein refers to a communications interface circuit and related components for digitally interfacing different electronic devices. Examples of interface buses include, but are not limited to, Universal Serial Bus (USB) interfaces, Firewire interfaces, other serial or parallel interfaces, as well as other computer or digital data interfaces known or developed in the art.

The term "electronics module" as used herein relates to a module including electronic components for providing the control and signal processing and related functions as described herein in conjunction with a pipe inspection system cable drum assembly and/or video camera head. An electronics module may include analog circuits, digital circuits, mechanical and electronic hardware, firmware stored in a programmable memory or device, and/or software components stored on a non-transitory medium, which may be mounted or disposed on or in one or more printed circuit boards or other circuit elements and related mechanical assemblies. An electronics module may use one or more processing elements to perform signal processing and related functions, and may further include analog signal conditioning circuits, as well as analog or digital circuits to receive and send data or information within a camera controller platform and/or externally to or from the camera controller platform. Additional components, such as keypads, displays, switches, sensors, memory devices, input/output devices, wired, radio, and/or optical interface modules, sensors, position determination modules, such as GPS or other location-identification modules, inertial location devices, or other elements such as are described herein may be included in or coupled to electronics modules in various implementations.

The word "exemplary" is used herein to mean "serving as an example, instance, or illustration." Any aspect and/or embodiment described herein as "exemplary" is not necessarily to be construed as preferred or advantageous over other aspects and/or embodiments.

Overview

This disclosure relates generally to portable pipe inspection systems and related accessories and apparatus. More specifically, but not exclusively, the disclosure relates to portable camera controller platforms for use with a pipe inspection system.

In accordance with aspects of the present disclosure, a camera controller platform may include elements configured for the rapid mounting and connection of a display device, such as an electronic computing device such as a laptop or notebook computer, as well as for enabling such a display device to be conveniently used as a pipe-inspection system monitor and a virtual control interface. The camera controller platform may additionally include an input device, such as a control keyboard or other input device, and may optionally include a built-in manual user interface device, such as, for example, a mouse joystick, or magnetic user interface device. Alternatively, a plurality of virtual controls may be supported by a software application installed on, or accessed by, the laptop, which may be connected to the camera controller platform by an interface bus such as a USB bus or other interface bus configuration.

For example, in one aspect, the disclosure relates to a pipe inspection system including a portable camera controller platform. The pipe inspection system may include, for example, a camera head coupled to the end of a push-cable, and a cable storage drum. The pipe inspection system may further include, for example, a camera controller platform, which may include a base assembly or base structure configured for mounting to a support element of the cable storage drum. The pipe inspection system may further include, for example, an electronic computing device, such as a computer or display device, which may be mounted to the platform base. The camera controller platform may include, for example, a user interface device or element to provide data exchange between the camera head and display device. The interface may include, for example, a front panel configured with a control keypad, touchscreen, or other user interface element, such as a magnetic user interface device.

In another aspect, the disclosure relates to a camera controller platform system. The camera controller platform system may include, for example, a fastener for securing an electronic computing device, such as a laptop computer or other display device, onto the base platform. The device may be secured using a capstan. The camera controller platform system may further include, for example, at least one rotatable and/or extendable platform extension wing. The camera controller platform system may further include, for example, a processing element including a processor and a USB bus connected to the processor. The camera controller platform system may further include, for example, a system cable plug or connector for connecting the platform to an interface circuit coupled to the cable storage drum and a camera head, using a system connector cable. The camera controller platform system may further include, for example, a control pad on a user interface for providing control commands to the camera head. Programming may be stored at least partially in firmware in the platform, enabling the control pad to interact with the pipe inspection system and laptop computer or other electronic computing system.

In another aspect, the disclosure relates to a man-portable control platform which allows a laptop computer to be removably mounted and electrically connected to a pipe inspection system. The camera controller platform may include folding and/or retractable platform wings to provide flexibility and increased surface area by being moved or withdrawn or retracted during use. A capstan assembly may be used to secure the laptop computer to the camera controller platform, which may be readily and removably attached to a cable storage drum or other pipe inspection device or system. The platform may include an input device, such as a control keyboard and/or an optional built-in mouse or other manual user interface device, allowing it to be used as a direct controller of the camera head. One or more virtual controls may be implemented in conjunction with a software application installed on, or accessed by, the laptop computer, which may be connected to the controller by a USB bus or other interface configuration, thereby allowing for flexible configuration of the pipe inspection system. In one aspect, the disclosure relates to a portable camera controller platform. The platform may include, for example, a base assembly configured to mechanically couple the platform to a pipe inspection system including a cable reel drum assembly and a camera head. The base assembly may be configured to be fully or partially integrated with the cable reel drum assembly. The platform may further include a user interface panel disposed on or in the base assembly. The platform may further include an electronics module coupled to the user interface panel. The electronics module may include one or more processing elements configured to receive control input signals from the user interface panel and provide control data the pipe inspection system. The processing element(s) may be further configured to receive one or more pipe inspection output signals from the pipe inspection system and provide data corresponding to the pipe inspection output signals to an electronic computing system.

The platform may further include, for example, one or more wings coupled to the base assembly. The one or more of the wings may be folding wings. The one or more wings may be retractable into the base assembly. The platform may further including a Universal Serial Bus (USB) hub coupled to the electronics module. The platform may further include a system connector coupled to the electronics module for receiving signals from a system cable connected to the pipe inspection system. The platform may further include a wireless communication module coupled to the electronics module for receiving wirelessly communicated signals from the pipe inspection system and/or for sending wireless communication signals to the pipe inspection system, such as to an interface module. The platform may further include a hub or router configured to wirelessly provide information to or from the pipe inspection system. The hub or router may be further configured to provide wired information to or from the pipe inspection system. The information provided from the hub or router may include images or video signals. The information may also include audio or video signals or data. The information may also include location, position, or orientation data or information. The information may also include control or feedback data or information. The information may also include sensor or actuator data or information.

The platform may further include, for example, a capstan assembly and a tensioning element configured to secure an electronic computing device to the platform. The capstan assembly may be further configured to limit the torque applied to the electronic computing device when secured to the platform. The capstan assembly may include tooth and spring elements to limit the applied torque.

The pipe inspection output signals may, for example, be video signals. The video signals may be converted to digital signals in accordance with an interface bus standard. The video signals may be compressed. The interface bus may be a Universal Serial Bus (USB).

The platform may further include, for example, a microphone. The electronics module may be further configured to receive an audio signal from the microphone and associate the audio signal with the digital signals, such as with video or images. The output signals from the pipe inspection system may be video signals, and the video signals may be compressed before being provided to the electronic computing system.

In another aspect, the disclosure relates to a pipe inspection system. The pipe inspection system may include, for example, a cable reel drum assembly, a push-cable coupled to the cable-reel drum assembly, a camera head coupled to a distal end of the push-cable, and an interface circuit configured to electronically couple the camera head to a first end of a system cable. The pipe inspection system may further include a camera controller platform. The platform may include a base assembly configured to mechanically couple the platform to a pipe inspection system including a cable reel drum assembly and a camera head, a user interface panel disposed on or in the base assembly, and an electronics module coupled to the user interface panel. The electronics module may include one or more processing elements configured to receive control input signals from the user interface panel and provide control data the pipe inspection system, and receive one or more pipe inspection output signals from the pipe inspection system and provide data corresponding to the pipe inspection output signals to an electronic computing system. The system may further include a a system connector coupled to the electronics module and to a second end of the system cable. The platform may be incorporated at least in part into the cable reel drum assembly.

In another aspect, the disclosure relates to a camera controller platform. The platform may include, for example, a base assembly, a user interface panel disposed on or in the base assembly, and an electronics module coupled to the user interface panel. The electronics module may include one or more processing elements. The processing elements may be configured to receive control input signals from the user interface panel and provide control data to a pipe inspection system, and receive one or more pipe inspection output signals from the pipe inspection system and provide data corresponding to the pipe inspection output signals to an electronic computing system.

In another aspect, the disclosure relates to a pipe inspection system. The pipe inspection system may include, for example, a cable reel drum assembly, a push-cable coupled to the cable-reel drum assembly, a camera head coupled to a distal end of the push-cable, and an interface circuit configured to electronically couple the camera head to a first end of a system cable. The pipe inspection system may further include a camera controller platform. The platform may include a base assembly, a user interface panel disposed on or in the base assembly, an electronics module coupled to the user interface panel. The electronics module may include one or more processing elements configured to receive control input signals from the user interface panel and provide control data the pipe inspection system, and receive one or more pipe inspection output signals from the pipe inspection system and provide data corresponding to the pipe inspection output signals to an electronic computing system. The pipe inspection system may further include a system connector coupled to the electronics module and to a second end of the system cable.

In another aspect, the disclosure relates to methods and processing for implementing the camera system functionality as described above, in whole or in part.

In another aspect, the disclosure relates to means for implementing the above-described methods and/or system or device functions, in whole or in part.

In another aspect, the disclosure relates to computer-readable media including instructions for causing a computer or processing element to implement the camera system functionality described above, in whole or in part.

Various additional aspects, features, and functionality are further described below in conjunction with the appended Drawings.

Various aspects and details of pipe inspection system devices, configurations, and methods which may be used in embodiments of the present invention in conjunction with the disclosure herein are described in co-assigned patent applications, including, for example, U.S. Patent Application Ser. No. 61/559,107, entitled PORTABLE PIPE INSPECTION SYSTEMS AND APPARATUS, filed Nov. 13, 2011, U.S. patent application Ser. No. 13/214,208, entitled ASYMMETRIC DRAG FORCE BEARINGS FOR USE WITH PUSH-CABLE STORAGE DRUMS, filed Aug. 21, 2011, U.S. Patent Application Ser. No. 61/430,932, entitled PORTABLE CAMERA CONTROLLER PLATFORM FOR USE WITH PIPE INSPECTION SYSTEM, filed on Jan. 7, 2011, U.S. patent application Ser. No. 12/704,808, entitled PIPE INSPECTION SYSTEM WITH REPLACEABLE CABLE STORAGE DRUM, filed Feb. 12, 2010, U.S. patent application Ser. No. 12/399,859, entitled PIPE INSPECTION SYSTEM WITH REPLACEABLE CABLE STORAGE DRUM, filed Mar. 6, 2009, U.S. patent application Ser. No. 12/371,540, entitled PUSH-CABLE FOR PIPE INSPECTION SYSTEM, filed Feb. 13, 2009, U.S. Provisional Patent Application Ser. No. 61/152,662, entitled HIGH PERFORMANCE PIPE INSPECTION SYSTEM, filed Feb. 13, 2009, and U.S. Provisional patent application Ser. No. 09/348,517, entitled VIDEO PIPE INSPECTION DISTANCE MEASURING SYSTEM, filed Jul. 7, 1999. The content of each of these applications is hereby incorporated by reference herein in its entirety for all purposes. These applications may be denoted collectively herein as the "Pipe Inspection System Applications."

Various aspects of manual user interface device apparatus, devices, configurations, and methods that may be used in conjunction with the platform embodiments of the disclosure herein are described in U.S. Utility patent application Ser. No. 13/310,670, filed Dec. 2, 2011, entitled MAGNETICALLY SENSED USER INTERFACE APPARATUS AND DEVICES, U.S. Utility patent application Ser. No. 13/292,038, filed Nov. 8, 2011, entitled SLIM PROFILE MAGNETIC USER INTERFACE DEVICES, U.S. Utility patent application Ser. No. 13/272,172, filed Oct. 12, 2011, entitled MAGNETIC THUMBSTICK USER INTERFACE DEVICES, U.S. Utility patent application Ser. No. 13/214,209, filed Aug. 21, 2011, entitled MAGNETIC SENSING USER INTERFACE DEVICE METHODS AND APPARATUS, and U.S. Utility patent application Ser. No. 13/110,910, filed May 18, 2011, entitled USER INTERFACE DEVICES, APPARATUS, & METHODS. The content of each of these applications is hereby incorporated by reference herein in its entirety for all purposes. These applications may be denoted collectively herein as the "User Interface Device Applications."

The following exemplary embodiments are provided for the purpose of illustrating examples of various aspects, details, and functions of apparatus, methods, and systems for inspecting the interior if pipes, conduits, and other voids; however, the described embodiments are not intended to be in any way limiting. It will be apparent to one of ordinary skill in the art that various aspects may be implemented in other embodiments within the spirit and scope of the present disclosure.

EXAMPLE EMBODIMENTS

Referring to FIG. 1, a camera controller platform embodiment 100 in accordance with aspects of the present disclosure is shown. Camera controller platform 100 may include a base assembly for providing mechanical coupling to additional pipe inspection system elements such as a cable reel assembly and camera head, electronic computing device such as a notebook or laptop computer, and/or other elements such as are described herein. In addition, platform 100 may include a user interface panel or element for receiving inputs from a user related to inspection operations such as cable reel deployment, camera orientation and control, pipe obstruction removal, display control, data or information storage, retrieval, or transmission, or other related functions.

In addition, platform 100 may include one or more electronics modules for receiving inputs from users or other components such as the camera head, microphones, sensors, or other input elements, providing input signal processing, interfacing between components, providing control, data and information storage, and/or other electronic, processing, storage, or data and information transmission functions such as are described herein. For example, images and video data or information, such as compressed digital video or other data or information, may be stored in the electronics module and/or in the electronic computing device or other device or system. Other information or data, such as control data or information, audio data or information, sensor data or information, environmental data or information, location data or information (e.g., position coordinates, such as may be obtained from inertial sensors, GPS modules, etc. that may be included in the camera control platform or other component of the pipe inspection system), or other data or information. The electronics modules may include one or more processing elements as well as associated components such as analog or digital circuit, input/output circuits, power supply circuits, video and audio circuits, sensor circuits, GPS or other location determination devices, inertial navigation devices, as well as other electronic circuits such as those described subsequently herein. Camera controller platform 100 may be configured to be coupled to pipe inspection apparatus and systems such as are described in the Pipe Inspection System Applications, incorporated by reference herein.

In an exemplary embodiment, a base assembly of platform 100 may include a front panel 102, a rear panel 106, a front platform 108, and a rear platform 110 such as shown in FIG. 1. A user interface panel may be mounted or coupled to one of the panels, such as to front panel 102 as shown. An exemplary user interface panel may include a keypad element such as keypad 104. Alternately, or in addition, the user interface panel may include mechanical or electronic key assemblies, joysticks or user interface devices which may be, for example, manual user interface devices as described in the User Interface Device Applications, and/or other input elements such as LCD touch screen panels and the like. In some embodiments other devices, such as a smart phone, tablet device, or other input device may be used as a user interface device. In addition, in some embodiments, an electronic computing device such as a notebook or laptop computer as described herein may also be used to provide user interface panel functionality in place of, or in addition to, keypad 104 or similar components.

The base assembly may further include one or more folding, bendable, and/or deployable/retractable wing elements. For example, in an exemplary embodiment, the base assembly of platform 100 may include a front folding wing 112 and a rear folding wing 114. In FIG. 1, the rear folding wing 114 is shown partially rotated toward an open position. The base assembly may further include additional mechanical and/or mounting components such as side panels 118 and 120 as shown in FIG. 2 and FIG. 3.

Figure 7:
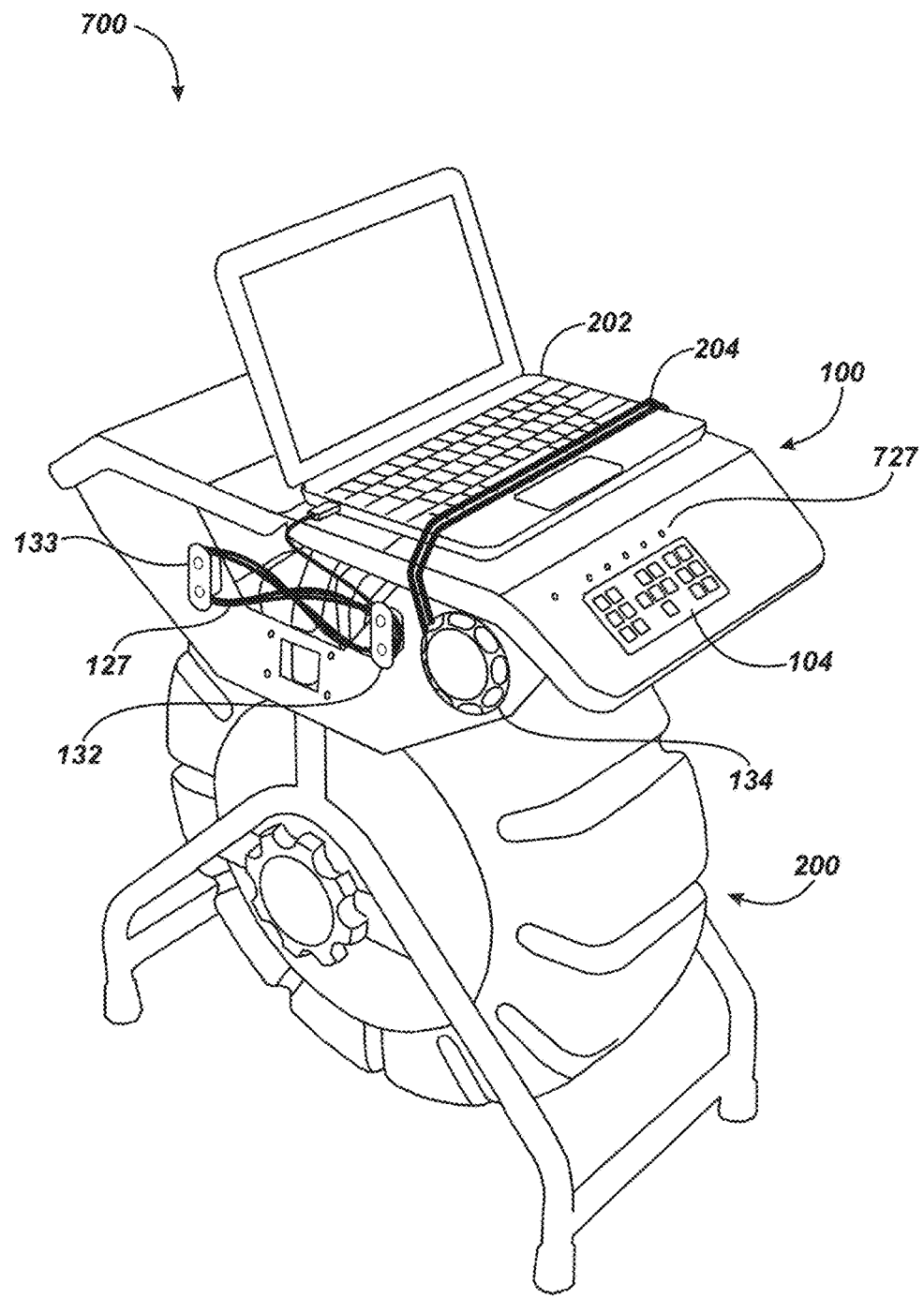
FIG. 7 illustrates details of an embodiment of a pipe inspection system.

A plurality of fasteners, such as screws 116, may be used to mount the front platform 108 and the rear platform 110, to right side panel 118 and left side panel 120 to form a shape suitable for mounting above or on a corresponding pipe inspection system. A strap anchor 122, which may be made of formed plastic or other materials may be disposed on the bottom edge of the right side panel 118 toward the forward end. A front right rubber foot 124 and a rear right rubber foot 126 may be disposed on the surface of the right side panel 118 with screws (not shown). An interface bus cable, such as USB cable 127, may be used to provide an electrical signal connection between the camera controller platform 100 and an electronic computing device, such as a laptop computer 202 (as shown in FIG. 7).

The camera controller platform 100 may include friction elements such as a front anti-slip mat 128 disposed on the surface of the front platform 108, a rear anti-slip mat 130 disposed on the surface of the rear platform 110, and/or an array of anti-slip squares 131 disposed on the surface of a surface of the front folding wing 112 and the rear folding wing 114.

Figure 2:
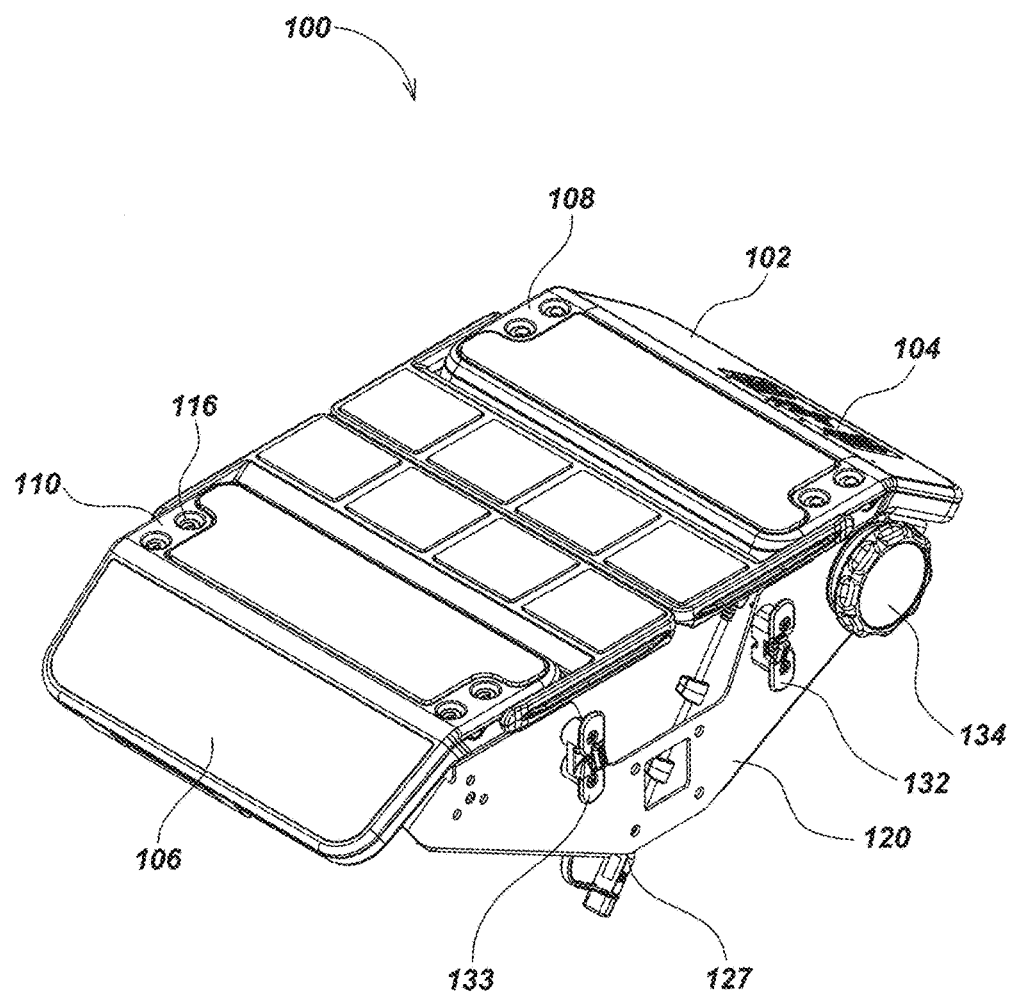
FIG. 2 is a perspective view illustrating details of the platform embodiment of FIG. 1.
Figure 3:
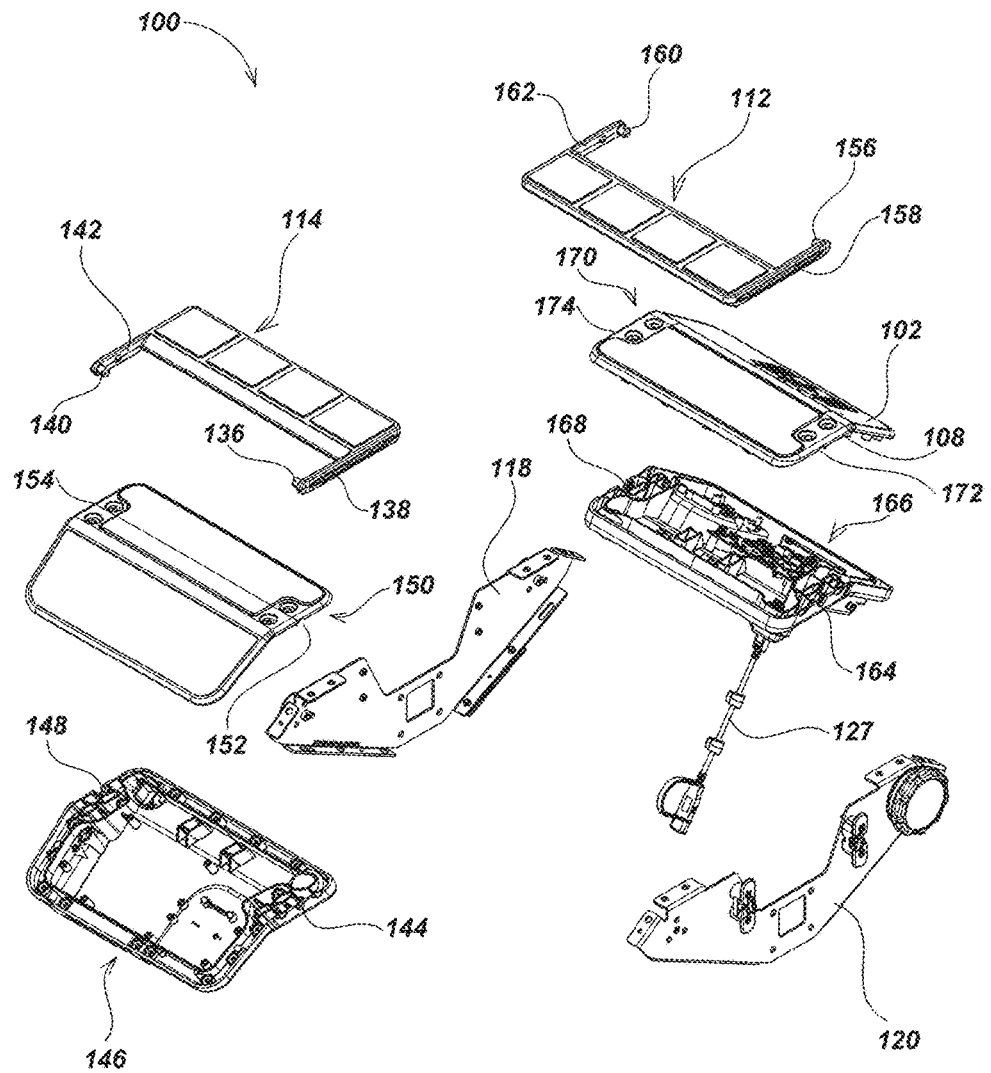
FIG. 3 is an exploded view of the platform embodiment of FIG. 1.
Figure 8:
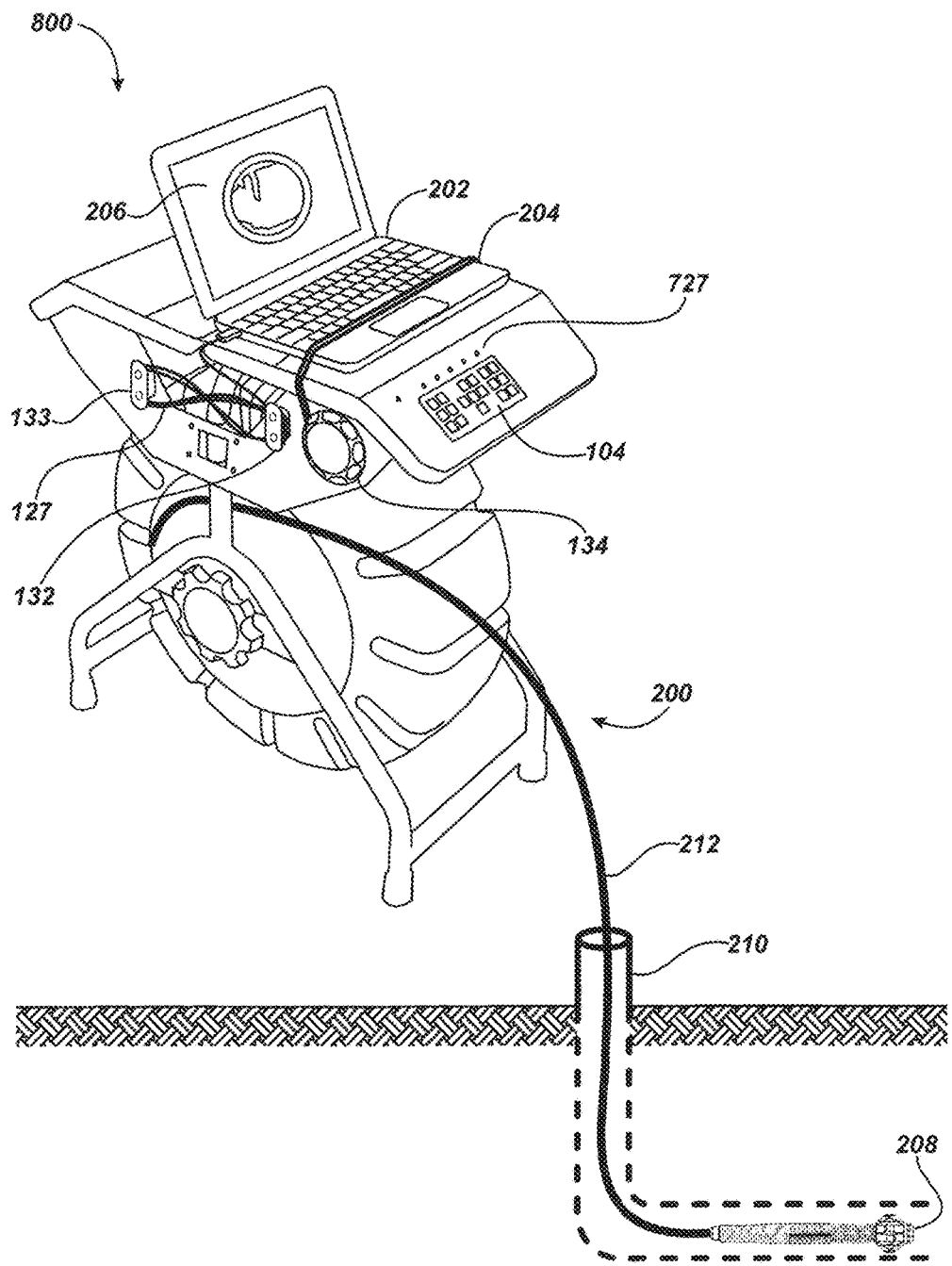
FIG. 8 illustrates details of an embodiment of a pipe inspection system in use.

Turning to FIG. 2, a left side perspective view illustrates additional details of the camera controller platform embodiment 100. The left side panel 120 may support a front cord wrap 132 and a rear cord wrap 133 for providing storage for the USB cable 127 which may be stored as shown in, for example, FIG. 7. A capstan may include a capstan knob or handle 134 disposed on the left side panel 120 of camera controller platform 100, which may be coupled to a capstan assembly 180, such as shown in FIG. 7 and FIG. 8, to provide a tensioning mechanism for a rubber elastic O-ring band 204 (as shown in FIG. 7 and FIG. 8) when securing a laptop computer 202 or other electronic computing device to the camera controller platform 100. The USB cable 127 is partially visible behind the left side panel 120, connected to a USB port 135 (not shown in FIG. 2).

FIG. 3 is an exploded view illustrating additional details of the camera controller platform 100 embodiment. The rear folding wing 114 may include a left rear molded hinge cylinder 136 and a right rear molded hinge cylinder 140, which may extend from the ends of a left rear arm 138 and a right rear arm 142, respectively. In assembly, the left rear molded hinge cylinder 136 and the right rear molded hinge cylinder 140 may each be seated into a left rear lower receptacle 144 and a right rear lower receptacle 148, respectively, which may be formed in a rear case bottom 146 of the base assembly.

A rear case top 150 may be formed with two outer surfaces, and may be positioned at an angle of approximately 30 degrees to one another, which may constitute the outer surface of the rear platform 110 and of the rear panel 106 (as shown in FIG. 1 and FIG. 2). A left rear upper receptacle 152 and a right rear upper receptacle 154 may each be disposed on the platform, such as on the inner surface of the rear case top 150 as shown. In assembly, left rear upper receptacle 152 and right rear upper receptacle 154 each mates with left rear lower receptacle 144 and right rear lower receptacle 148, respectively, which movably contains left rear molded hinge cylinder 136 and right rear molded hinge cylinder 140 to provide a flexible hinge.

Still referring to FIG. 3, the front folding wing 112 may include a left front molded hinge cylinder 156 extending from the end of a left front arm 158 and a right front molded hinge cylinder 160 extending from the end of a right front arm 162. In assembly, left front molded hinge cylinder 156 may be seated into a left front lower receptacle 164 disposed on a front case bottom 166. Likewise, right front molded hinge cylinder 160 may be seated into a right front lower receptacle 168 disposed on the front case bottom 166.

A front case top 170 may be formed with two outer surfaces, and may similarly be configured at an angle of approximately 30 degrees to one another, which may provide an outer surface of the front platform 108 and of the front panel 102. The inner surface of the front case top 170 may include a left front upper receptacle 172 which mates, when assembled, with the left front lower receptacle 164, and movably contains the left front molded hinge cylinder 156 forming a left hinge. The inner surface of the front case top 170 may additionally include a right front upper receptacle 174 which mates, when assembled, with the right front lower receptacle 168 and movably contains the right front molded hinge cylinder 160, thus forming a right hinge.

Figure 4:
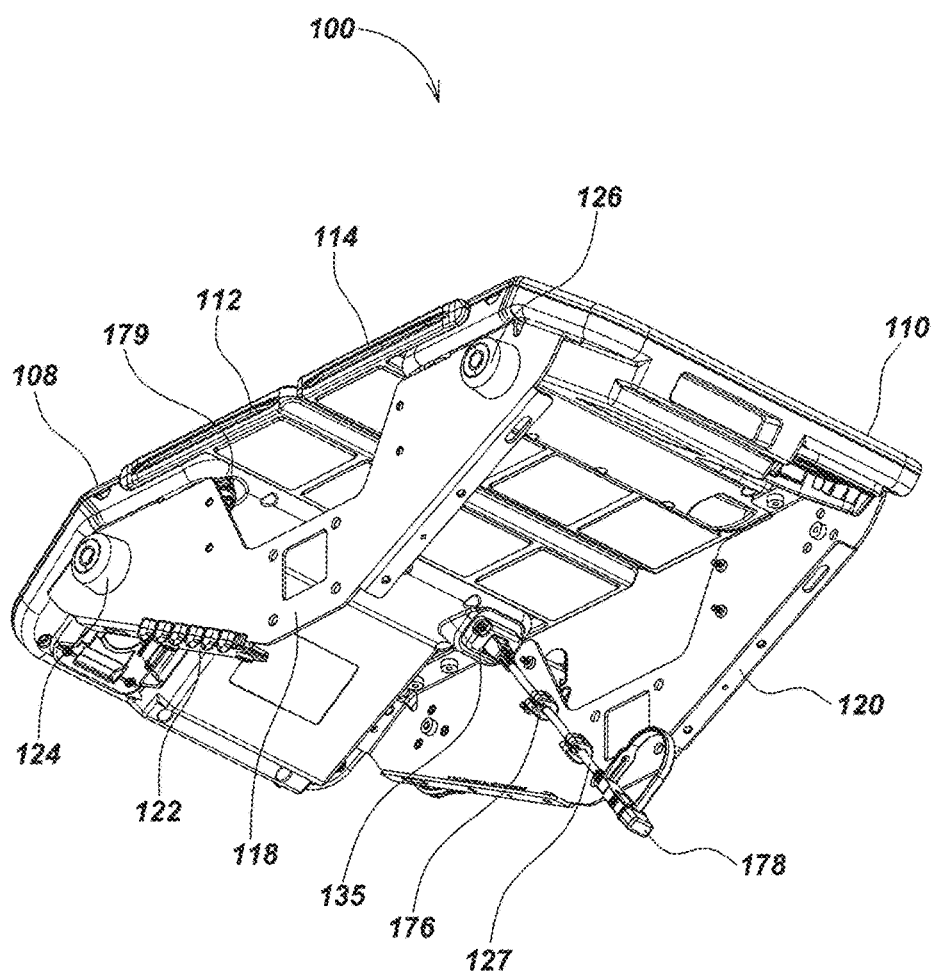
FIG. 4 illustrates details of the platform embodiment of FIG. 1, taken from the underside thereof.

Turning to FIG. 4, a lower right perspective view illustrates additional details of the camera controller platform embodiment 100. The front folding wing 112 and the rear folding wing 114 are shown in a closed position. When rotated to an open position, the front folding wing 112 extends the working surface of the front platform 108. When rotated to the open position, the rear folding wing 114 extends the working surface of the rear platform 110. Although wings 112 and 114 are shown in example embodiment 100 as folding wings, in other embodiments they may be configured to be retractable into the base assembly and/or may be both foldable and retractable.

The front platform 108 and the rear platform 110 may be coupled to the right side panel 118 and on the left side panel 120 such as shown in FIG. 4. The USB cable 127 may be electrically connected to the camera controller platform via the USB port 135, which may be further coupled to an electronics module (not shown). USB cable 127 may be equipped with a plurality of rubber cord clips 176, which may be used for storing USB cable 127, and a protective dust cap 178. The strap anchor 122 may be disposed on the front lower edge of the right side panel 118, and may be used for securing an electronic computing device such as laptop computer 202 (as shown in FIG. 7) into position. A system connection plug 179 that is partially obscured in FIG. 4, which may connect to a system cable 226, may be used to connect the camera controller platform 100 with a pipe inspection system element, such as a cable storage drum assembly 200 (as shown in FIG. 7) and/or with other related components, such as sondes, pipe clearance components, and the like. The system connection plug or connector may also be coupled to the electronics module for interfacing data and information signals to or from the pipe inspection system, such as video or image signals and data, control signals, cable deployment data, etc., with the electronics module, input device, and/or electronic computing device.

Figure 5:
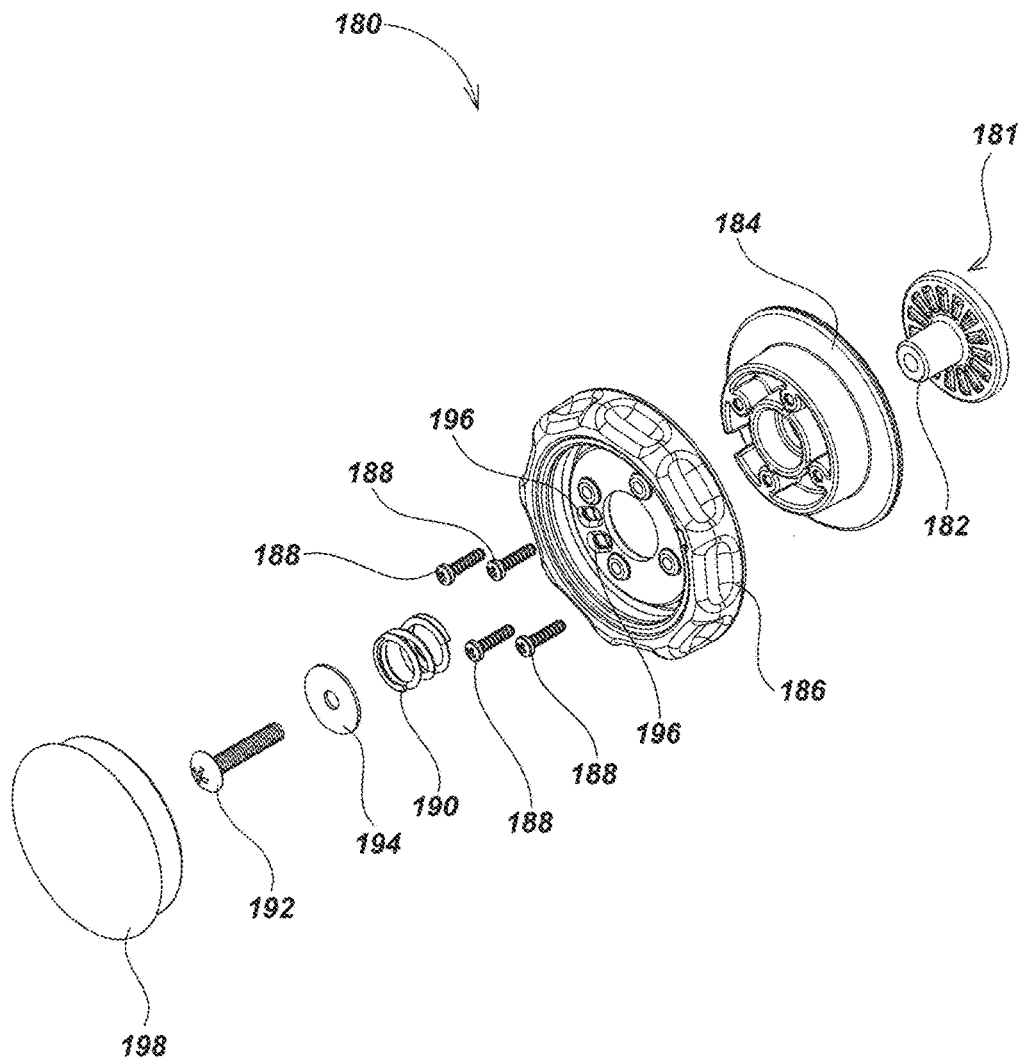
FIGS. 5 and 6 are enlarged exploded views of an embodiment of a capstan assembly.
Figure 6:
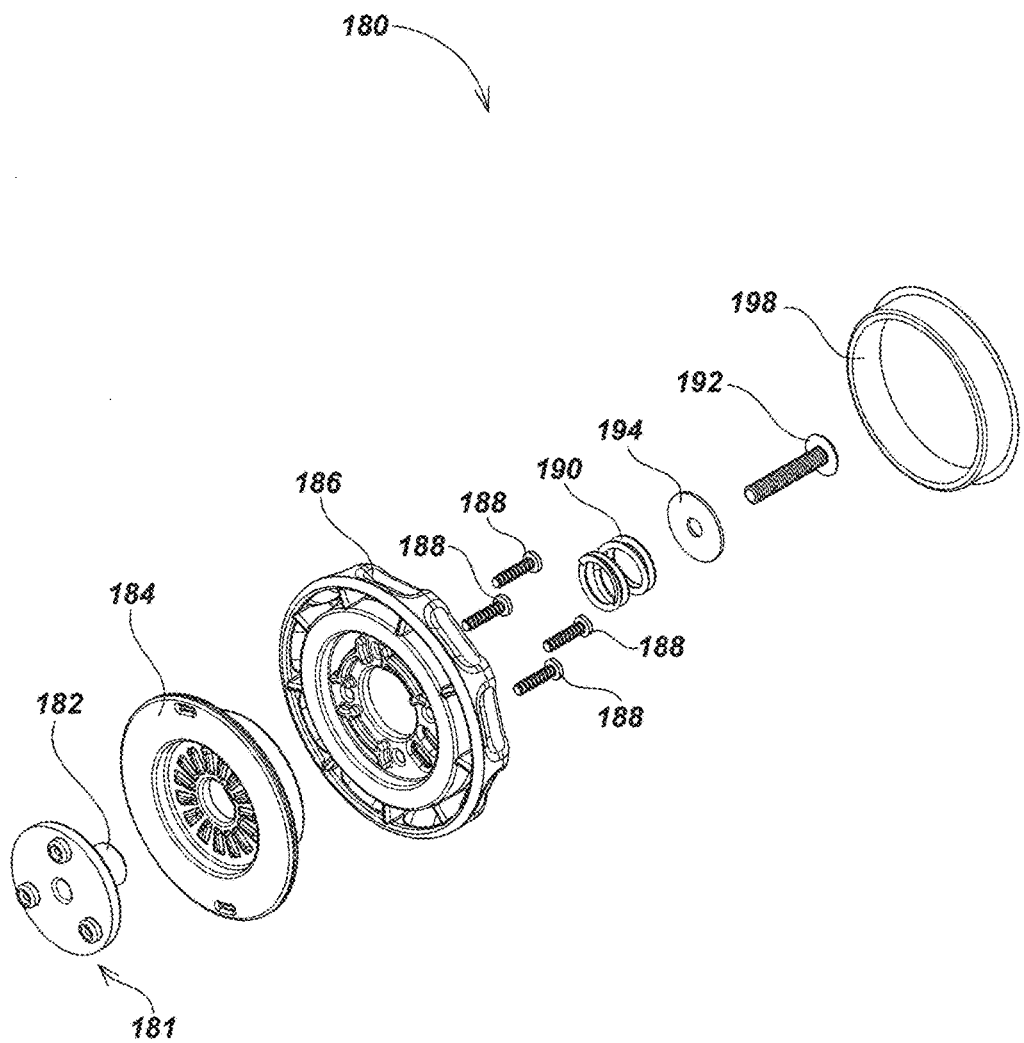

A camera controller platform such as platform embodiment 100 may include a capstan or ratcheting assembly to mechanically couple the electronic computing device to the platform. For example, as shown in FIGS. 5 and 6, an enlarged exploded view illustrates details of an embodiment of a capstan assembly 180, which may be coupled to capstan knob 134 as shown in FIG. 2. In one aspect, an adjustable ratchet or capstan assembly 180 may be used to tighten a flexible tensioning element, such as a rubber elastic O-ring band 204 (as shown in FIG. 7), to secure a laptop computer 202 or other electronic computing device to camera controller platform 100.

A toothed bottom plate 181 with a molded central conical frustum 182 may be seated in a central opening in a molded ratchet base 184, the inner surface of which may have a toothed pattern which complements the tooth pattern in the toothed bottom plate 181. A ratchet grip 186 may be coupled to the molded ratchet base 184 with a plurality of screws 188. A pressure spring 190 may be retained in the central opening of the ratchet grip 186 with a bolt 192 and a washer 194. The pressure spring 190 exerts pressure against the molded ratchet base 184, causing the formed teeth on its lower surface to marry with the grooves between the teeth of the toothed bottom plate 181. Rotating the ratchet grip 186 causes the formed teeth on the lower surface of the molded ratchet base 184 to ride up over the teeth of the toothed bottom plate 181, against the force imposed by the pressure spring 190, and thereafter to marry in the next available groove between the teeth of the toothed bottom plate 181. A plurality of oval openings 196 may be disposed on inner surface of the ratchet grip 186, around its central opening. In use, a rubber elastic O-ring band 204 (not shown in FIGS. 5 and 6) may be stretched lengthwise and anchored to the ratchet mechanism by being led through the oval openings 196 and then through its own loop, thus securing it to the ratchet grip 186. The ratchet grip 186 is sealed with a plastic plug 198. The capstan knob 134, as shown in FIGS. 2 as 3, may include the ratchet grip 186 and the plastic plug 198, which cover and retain the other elements of the capstan assembly 180.

The combination of the tooth design and the spring load in the capstan may be configured to limit the torque that the capstan assembly can react to, concomitantly limiting the achievable tension in the O-ring cord (as when stretched across the laptop) to avoid damage to the laptop or other electronic computing device. By appropriate selection of these parameters, the designer can reduce the potential for a user to over-tighten the O-ring cord and damage the laptop secured thereby. In some embodiments, a tensioning mechanism (not shown) may be included to allow a user to select the tension to be applied by the capstan or ratcheting assembly.

FIG. 7 and FIG. 8 illustrate details of an embodiment 700 of a platform coupled pipe inspection system, which may include elements such as a cable storage drum 200 of a pipe inspection system, a camera controller platform, such as platform embodiment 100, an electronic computing device, such as laptop 202, and an interface bus cable, such as USB cable 127, as well as LED status indicators 727. Various elements of the system 700 may be constructed in accordance with details of pipe inspection system and system and apparatus embodiments described in the Pipe Inspection System Applications.

In one aspect, the camera controller platform 100 may be configured to be mounted to a frame 750 of the pipe inspection system, which supports cable storage drum 200. The mounting may be configured to allow the platform to be readily attached and detached, such as through use of pins, bolts, knobs with wing nuts, and the like. The mounting may also be configured to allow the platform to rotate relative to the pipe inspection system to allow a user to adjust the platform and notebook orientation.

FIG. 8 illustrates details 800 of the inspection system embodiment of FIG. 7 in use. The cable storage drum 200 may be used to carry multiple coils of a resilient flexible push-cable 212 (shown partially deployed) whose distal end may be operatively connected to a camera head 208. In operation, a user will pay out the push-cable. For example, by rotating the drum push-cable 212 may be deployed and the attached camera head 208 is then forced down a pipe 210. Excess USB cable 127 may be stowed on the front cord wrap 132 and the rear cord wrap 133 as shown.

The rubber elastic O-ring band 204 may be internally anchored to the ratchet grip 186 (as shown in FIG. 5 and FIG. 6), and may be led over the laptop computer 202 and secured to the strap anchor 122 (as shown in FIG. 1 and FIG. 4). By gripping and rotating the capstan knob 134, the operator may increase or decrease the tension on the rubber elastic O-ring band 204 as the rubber elastic O-ring band 204 is wrapped around the base of the capstan assembly 180 (FIGS. 5 and 6) or released there from. In use, a system cable (not shown) of the pipe inspection system may be connected to the camera controller platform 100 through a system connection plug 179 (as shown in FIG. 4), thereby allowing control of the camera head 208 from the laptop computer 202 or other electronic computing device and/or from the keypad 104 or other input device as needed.

A display screen 206 of the laptop computer 202 or other electronic computing device displays images or video as sensed by the camera head 208, thereby providing a view of the interior of the pipe 210 as seen at the distal end of the push cable 212. Control circuitry in the electronics module of camera controller platform 100 may be used for communicating with the laptop computer 202 and with the camera head 208. Images from the camera head 208 may be captured as individual photos or as video clips, and may be combined and recorded with audio commentary. This may be done by using a software application on the laptop computer 202 or other electronic computing device. The images and video clips may be stored on the laptop computer 202, in the electronics module, and/or on a removable storage device, such as, for example, a USB thumb drive or other memory or data storage device. Images and/or clips may also be formatted into reports to be electronically mailed, printed, delivered by thumb-drive or DVD, or played back for a customer's education from the laptop computer 202.

Figure 9A:
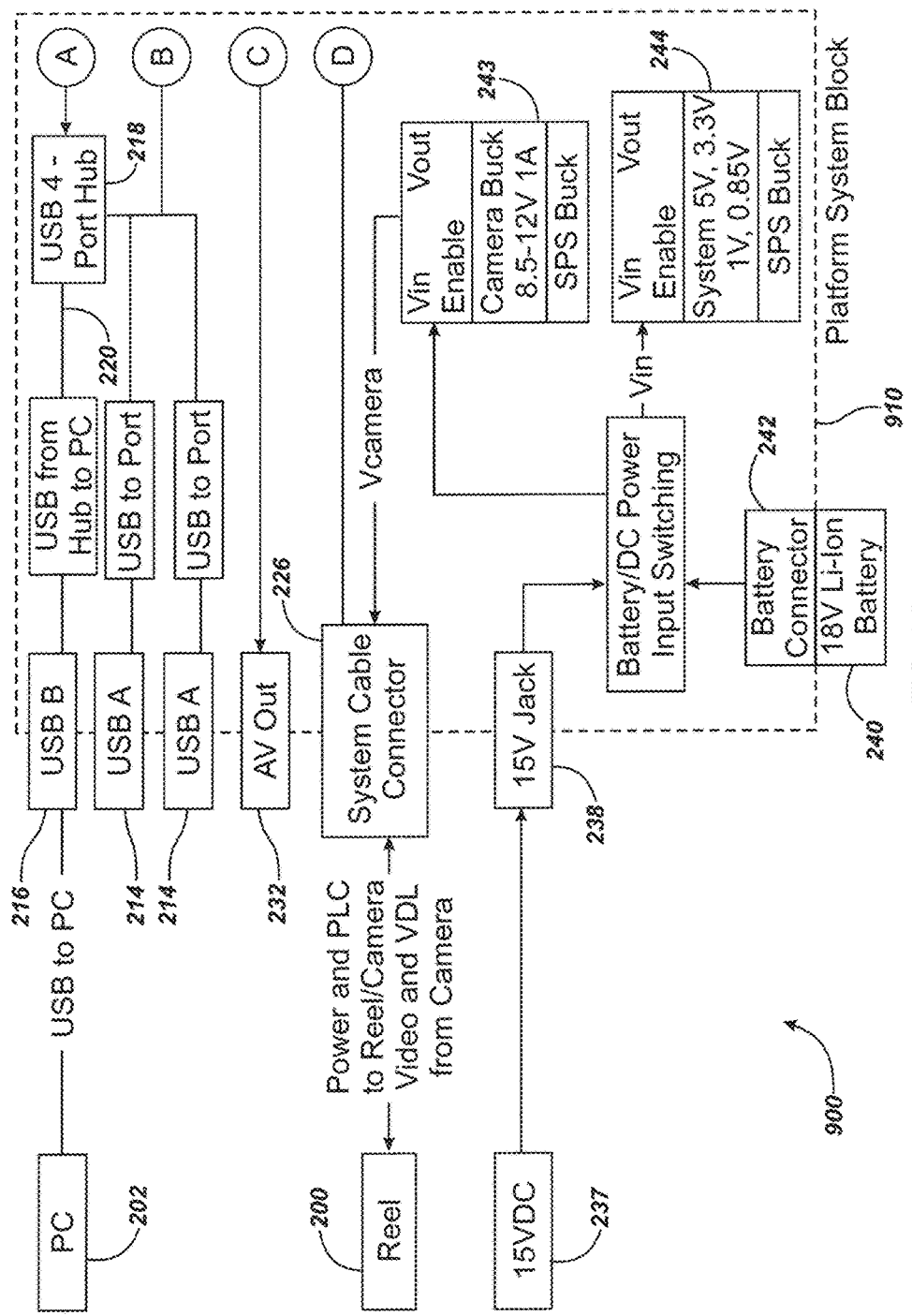
FIGS. 9A and 9B are block diagrams illustrating details of an embodiment of a portable camera controller platform.
Figure 9B:
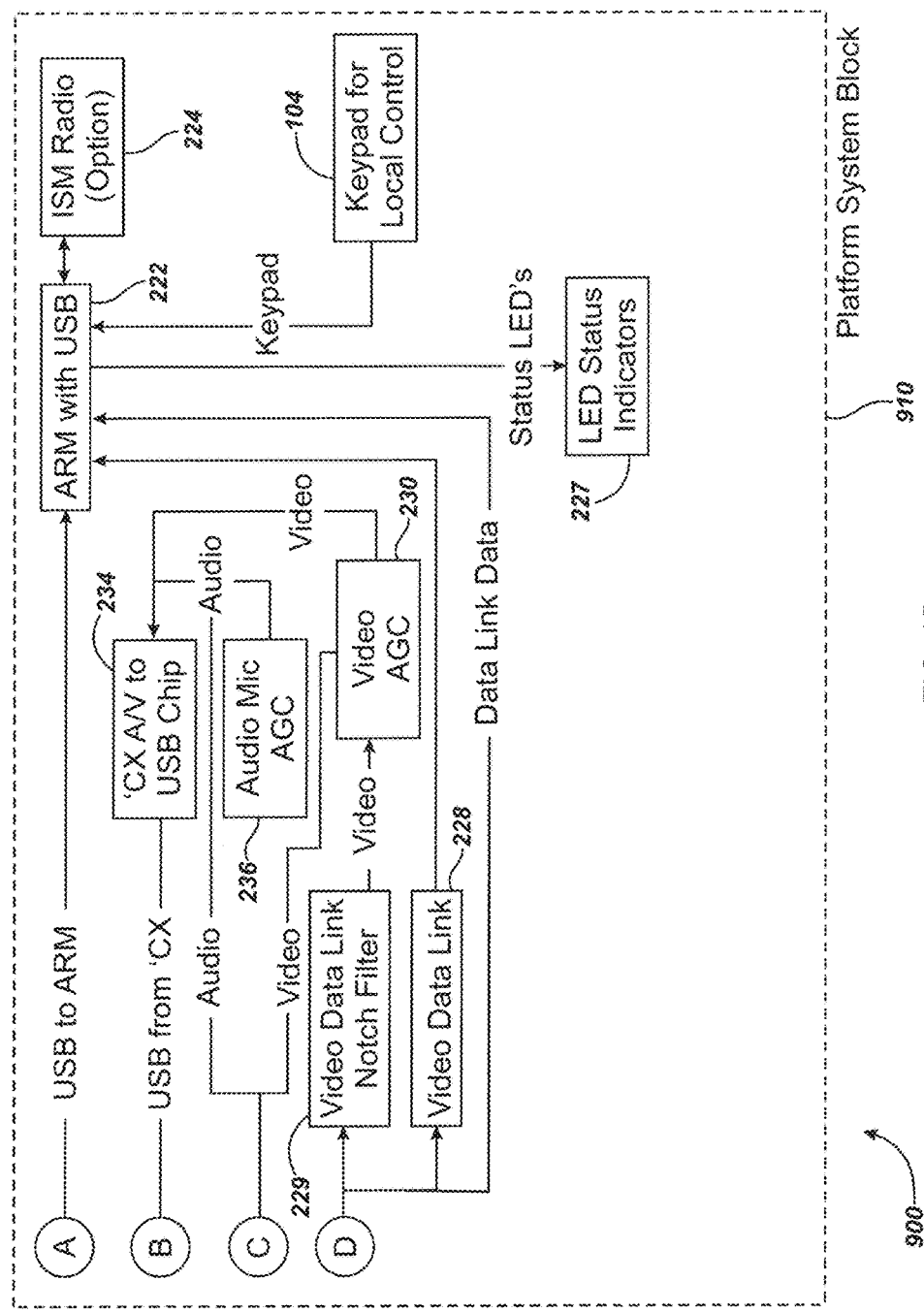

Turning to FIGS. 9A and 9B, a block diagram illustrates details 900 of electronic signaling elements in a pipe inspection system such as the system illustrated in FIG. 7. A platform system block embodiment 910, which may be implemented in whole or part in an electronics module as described herein, illustrates example detail of circuitry and signal processing in a camera controller platform, such as the camera controller platform 100 shown in FIGS. 1-4 and 7. For example, camera controller platform embodiment 100 may be electrically coupled to interface bus ports, such as one or more USB ports, such as for example, a pair of computer USB ports A 214, and one of a computer USB port B 216 of a USB hub 218 connected with a USB port 135 (as shown in FIG. 4) of the camera controller platform 100, and a USB bus 220.

In use, the USB cable 127 may be connected to the computer USB port B 216 and to the laptop computer 202. Two external USB plugs may allow external USB devices, such as memory thumb-drives or other USB devices, to be connected to each of the computer USB ports A 214. A processing element of the electronics module, which may include, in an exemplary embodiment, a central ARM processor 222, may be configured to control data transmission to, and data receipt from, the USB bus 220 (or other interface bus). The ARM processor 222 may receive communications from an optional ISM-band wireless link 224 or other wireless communications module, such as a WI-FI, Cellular Data, WI-Max, Bluetooth, cellular, or other wireless communications module.

The ARM processor may additionally be configured to receive data link transmissions from a pipe inspection system via an associated system cable 226, which may be connected, in use, to the platform's system connection plug 179 (as shown in FIG. 4). Various aspects and details of system cables and connectors, as well as connections to a cable storage drum or related systems to transfer video information and data are described in, for example, U.S. patent application Ser. No. 12/704,808, filed Feb. 12, 2010, entitled PIPE INSPECTION SYSTEM WITH REPLACEABLE CABLE STORAGE DRUM, and U.S. patent application Ser. No. 10/061,887 (now U.S. Pat. No. 6,958,767), filed Jan. 31, 2002, entitled VIDEO PIPE INSPECTION SYSTEM EMPLOYING NON-ROTATING CABLE STORAGE DRUM, the contents of which are incorporated by reference herein in its entirety.

The ARM processor 222 may exchange control data and information, as well as other signals, data or information, with the camera controller platform input device, such as keypad 104, in addition to the electronic computing device, such as laptop 202. The ARM processor may additionally control the display of a plurality of LED status indicators 227 to provide visual displays of various operating conditions, such as, for example, remaining battery power, power status (e.g., on/off), connection and/or status of attached components such as sondes, microphone(s), sensors, or other input or output devices, and the like.

Still referring to FIGS. 9A and 9B, video and other data from the pipe-inspection system may be provided to the ARM processor 222 by means of a video data link 228, and video may also be passed through a video data link notch filter 229 and a video automatic gain control 230, and be sent to an AV out port 232. Video may alternatively be processed by a video and audio USB decoder 234 such as, for example, the Conexant Systems CX23100, and transmitted by way of USB bus 220 to the laptop computer 202 or other electronic computing device for display.

The camera controller platform may be configured to receive and record audio commentary provided from a user during a pipe-inspection, such as through use of an integral or external microphone or other audio sensor device. Audio, sensed by an onboard or external microphone may be processed through an audio automatic gain control block 236, and may similarly be passed directly to the AV out port 232, or passed through the video and audio USB decoder 234 and back to the laptop computer 202 or other electronic computing device for playback, storage, and/or transmission to other devices or system, such as via a wired or wireless connection.

Data exchanged between the laptop computer 202 and the camera controller platform and any peripheral devices may optionally be encrypted for enhanced security using software and/or hardware encryption devices (not shown) in the electronics module or electronic computing device.

Electrical power for the camera controller platform may be provided by an external 15 VDC power supply 237, which may provide, for example, 15V of direct current through a DC jack 238 on the platform. Alternately, or in addition, power may be provided by a removable battery, such as an 18V lithium-ion battery or other battery module that may be mounted to a battery connector 242. A power supply module, such as a buck converter switching power supply 243, may be used to supply camera voltage and provides 8.5 to 12 volts at approximately 1 amp to power the pipe-inspection system's camera head 208 via a cable and connector, such as system cable 226 and cable connector 179. A separate buck converter switching power supply 244 may be used to modify the supplied power to provide voltages of 0.85V, 1V, 3.3V, and 5V to the pipe-inspection system for other powering functions. Examples of battery pack apparatus and systems as may be used in embodiments of a platform such as platform 100 are described in, for example, U.S. Patent Application Ser. No. 61/501,172, filed Jun. 24, 2011, and U.S. Patent Application Ser. No. 61/521, 262, filed Aug. 8, 2011. The content of each of these applications is incorporated by reference herein in its entirety.

Turning to FIGS. 10A and 10B, a data table 1000 illustrates an embodiment of data links for use in communicating data and information in a pipe inspection system, such as system 700 as illustrated in FIG. 7. In one aspect, a tailored data structure may be used to provide messages between a pipe-inspection system, such as pipe inspection system 700 used with a camera controller platform, such as camera controller platform embodiment 100, an electronics module of the cameral controller platform, and an electronic computing device, such as laptop computer 202. Data connection elements and configurations, such as shown in FIGS. 9A and 9B, may be used to send and receive the signaled data. In an exemplary embodiment, the tailored data link may use the following messaging format:

| Data Link Communication | |
|---|---|
| Format | |
| Start Bit | (66% Duty ON) |
| Address Byte | 3-Bits --> "From" Node |
| | 3-Bits --> "To" Node |
| | 2-Bits --> Message Type |
| Data Bytes | 1-15 |
| Stop Bit | (33% Duty ON) |

| Data Link Communication | |
|---|---|
| Message Types | |
| Type | Value |
| Autonomous | 0 |
| Response | 1 |
| Query | 2 |
| Idle | 3 |

The interpretation of the data stream may be governed by hardware, software, and/or firmware in the camera controller platform 100, such as in the electronics module, and/or by application software installed on, or accessed by, the laptop computer 202 or other electronic computing device. Details of an embodiment of an example data link payload architecture are illustrated in FIGS. 10A and 10B. As shown in FIG. 10A and FIG. 10B, in an exemplary embodiment, the datalink payload may be divided into seven distinct types of data suitable to use in an pipe inspection system. Several of these data types relate to the counting of distance the push cable 212 has been extended into the pipe 210 (as shown in FIG. 8) during pipe inspection. Each data type may include a message ID of one byte, and each message type may include a one-byte checksum after its message content.

For example, count information 246 derived from a sensor built into the pipe inspection cable storage reel may be provided in centimeters and may be converted to feet and inches for local display purposes. Data may be provided from an interface circuit of the cable storage reel or related components, such as via a system cable. Raw count information 248 may include the total number of times the counting unit has been powered on, a stored value for a temporary intermediate zero point, and a current count. A Measurement Origin 250 message may be used to indicate whether present measuring is being done from an absolute start point such as when the system was powered on, or from a relative user-selected zero-point. In some applications the user may also be able to set an absolute zero point, such as the entry point of a pipe, for distance counting as well.

Odometer information 252 may provide a total count of footage extended from and returned into the reel since first activation. Reel information 254 may provides parametric data needed to convert reel rotation into linear distance, including the reel type, the length of total cable carried in the reel, and the cable type. The Raw Total Count information 256 may be a computed value based on the sum of variables under the Raw Count Information 248. Six bytes may be reserved for transmitting a software version 258 used by the counter. Additional fields and data types may be added depending on the application; for example, when sensors are built into the camera head to detect orientation and motion. Count information may be transferred between the various pipe inspection system components including the camera controller platform, electronic computing device, cable reel assembly, and/or external systems. Additional data or information, such as camera orientation, signal levels, and the like may be similarly provided.

Various aspects and details of implementations of apparatus, systems, and methods for providing counting, distance measurement, and related apparatus and functions are described in, for example, U.S. patent application Ser. No. 12/766,742, filed Apr. 23, 2010, entitled PIPE INSPECTION SYSTEM CABLE COUNTER AND OVERLAY MANAGEMENT SYSTEM, U.S. patent application Ser. No. 09/348,517 (now U.S. Pat. No. 6,545,704), filed Jul. 7, 1999, entitled VIDE PIPE INSPECTION DISTANCE MEASURING SYSTEM, U.S. patent application Ser. No. 11/928,818, filed Oct. 30, 2007, entitled PIPE MAPPING SYSTEM, U.S. patent application Ser. No. 11/774,462, filed Jul. 6, 2007, entitled MESH NETWORKED WIRELESS BURIED PIPE AND CABLE LOCATING SYSTEM, and U.S. patent application Ser. No. 12/399,858, filed Mar. 6, 2009, entitled PIPE INSPECTION SYSTEM WITH SELECTIVE IMAGE CAPTURE. The content of each of these applications is incorporated by reference herein in its entirety.

Figure 11A:
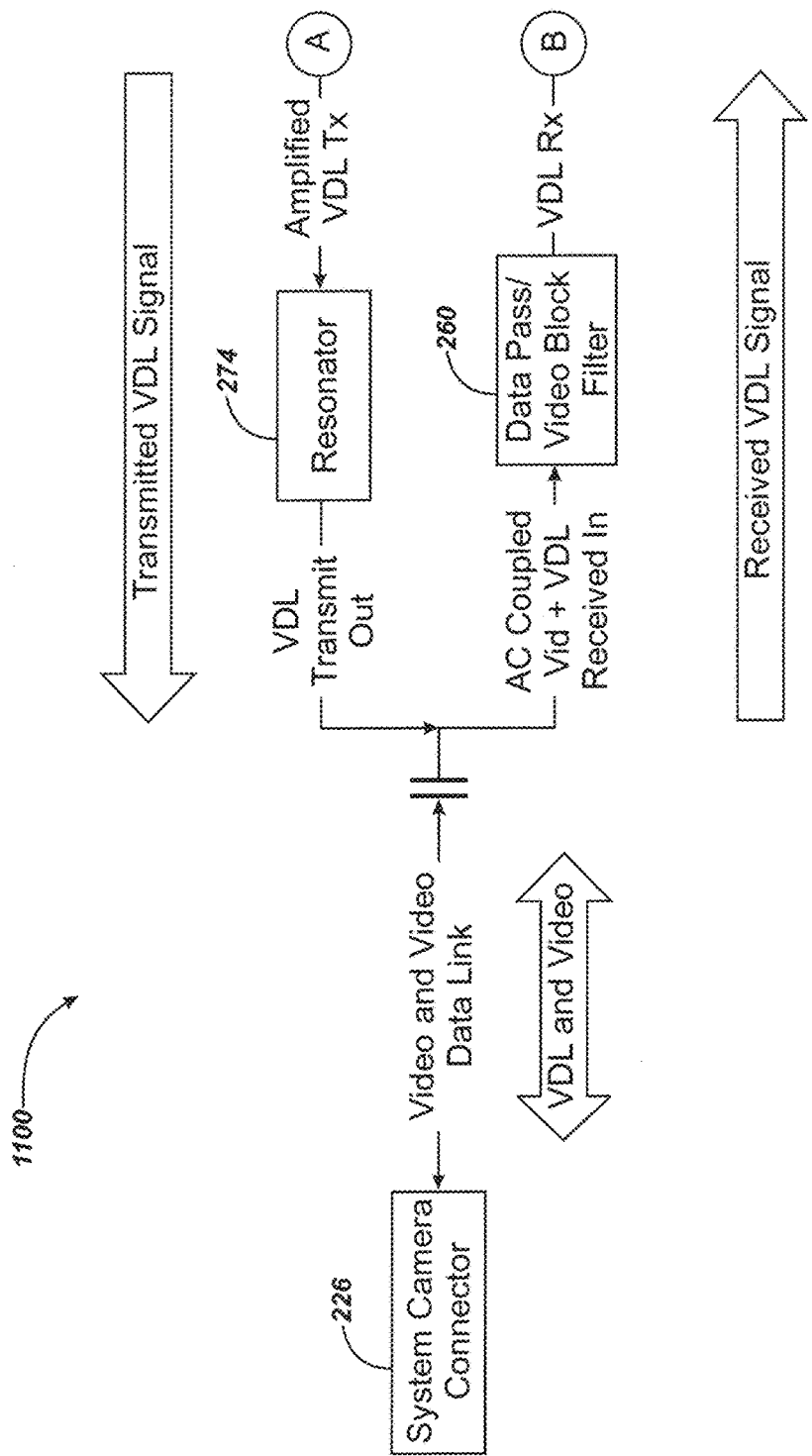
FIGS. 11A and 11B illustrate details of video data link signal processing of the portable camera controller platform.
Figure 11B:
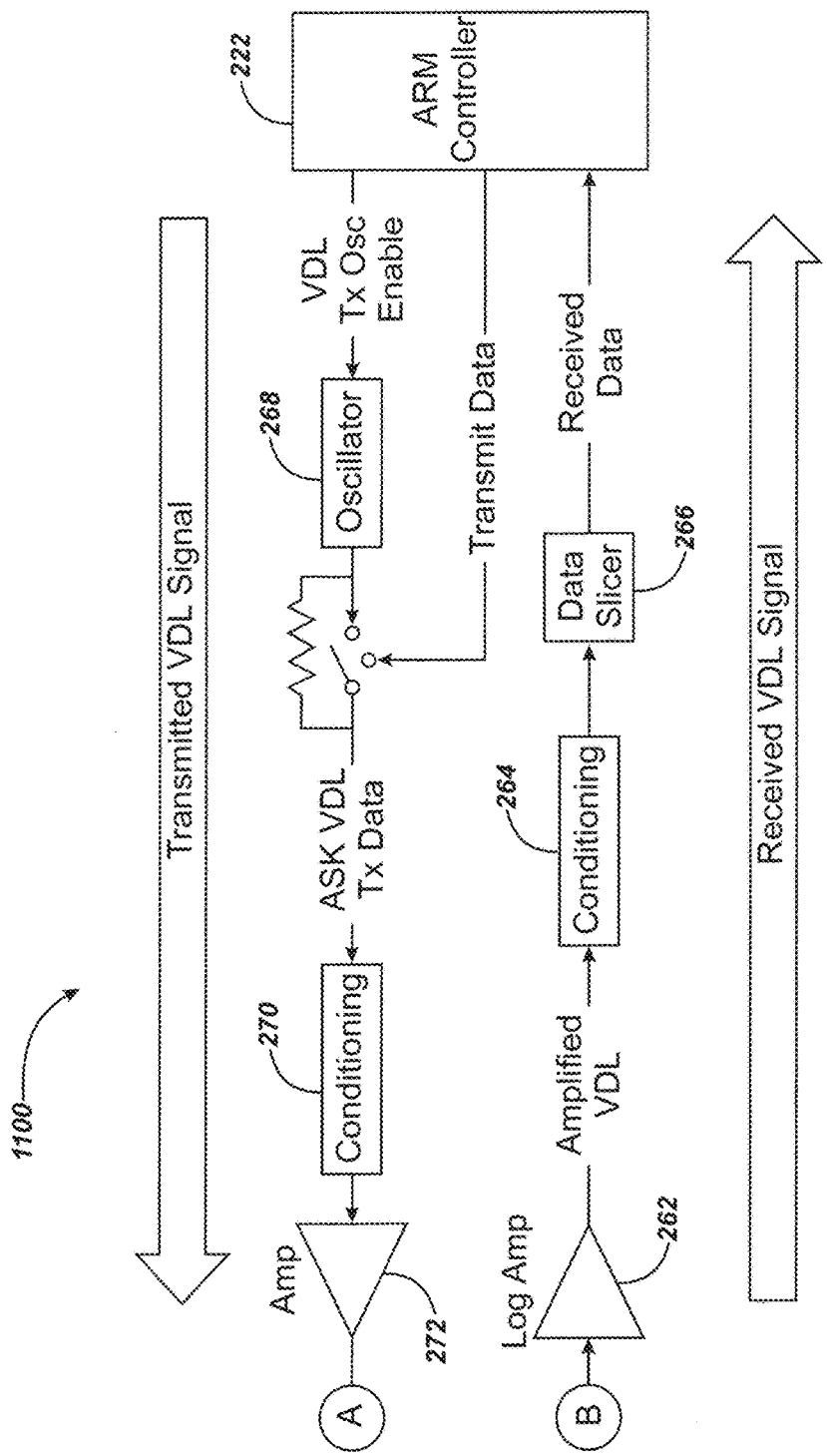

Turning to FIGS. 11A and 11B, details of an embodiment of signal processing of modulated data encoded with video are illustrated. The signal processing illustrated may be implemented in an electronics module which may include one or more processing elements along with related analog, digital, hardware, and/or software components to perform the functionality described herein. Such data may include, for example, information related to camera orientation, signal levels, as well as other data or information, such as sensor data from accelerometer or gyro sensors or other inertial navigation or related sensors, which may be disposed in the camera head. When coupled video and data is received from the system cable 226, such as through cable plug/connector 179, the video and data may be passed to a selective data band pass filter 260 which blocks video signals while passing data. The output data signal may then be amplified by an amplifier circuit 262 and conditioned by an adaptive filter 264. The data may then be detected and parsed by a data slicer 266 and passed to a processing element, such as the ARM processor 222, for further processing and output signal generation.

For transmitted data such as, for example, parametric settings, control data, and the like, the ARM processor 222 may configure and control an oscillator 268, which may then act as a carrier frequency in sending amplitude-shift keyed (ASK) data. ASK data is then passed through a transmit filter 270 and a transmit amplifier 272. A resonator 274 may be used to provide transmission impedance matching for data transmission to the pipe inspection system via, for example, the system cable 226.

Figure 12:
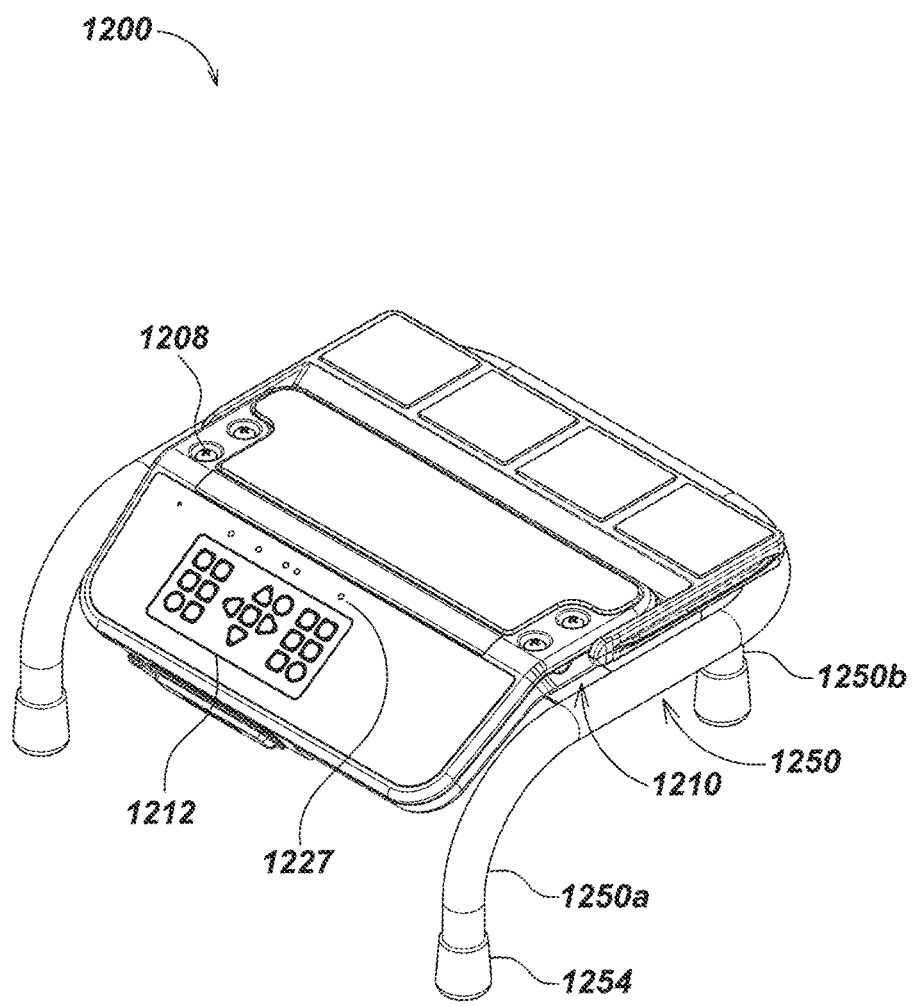
FIG. 12 illustrates details of an embodiment of a mini camera controller platform module.

FIG. 12 illustrates details of another embodiment of a camera controller platform, in this case in the form of a mini camera controller platform embodiment 1200. Platform embodiment 1200 may include similar components and functionality to that described previously with respect to embodiment 100. For example, platform embodiment 1210, which may include a user interface device, such as user interface panel 1212, may be mounted to a frame 1250 with one or more fasteners, such as screws 1208. Frame 1250 may include one or more legs, such as a pair of front legs 1250a and a pair of back legs 1250b to provide spacing between platform 1210 and the ground or floor surface. Front legs 1250a and/or back legs 1250b may be integrally formed with frame 1250. For example, legs 1250a may extend from the top surface of frame 1250, gradually curving downward and symmetrically. Back legs 1250b may be molded with frame 1250, extending downward symmetrically to form a right angle between legs 1250b and the top surface of frame 1250. A non-skid material 1254, such as textured rubber or other similar material may be disposed on the bottom surface of one or more legs 1250a and 1250b to prevent slippage. Platform 1210 may include one or more LED indicators 1227 to provide information related to parameters such as remaining battery power (e.g., as indicated by color), power on/off status, connection of other components such as sondes, etc., or other data or information.

Platform embodiment 1200 may be configured to be connected to a cable reel and/or other component of a pipe inspection system (not shown in FIG. 12), such as a sonde, and/or may be directly connected to a grounded transmitter (not shown in FIG. 12), and may optionally be mounted to the reel, depending on space constraints. Details of sonde and transmitter apparatus, systems and methods are described in, for example, U.S. patent application Ser. No. 10/268,641, filed Oct. 9, 2002, entitled OMNIDIRECTIONAL SONDE & LINE LOCATOR, U.S. patent application Ser. No. 12/902,551, filed Oct. 12, 2010, as well as U.S. patent application Ser. No. 12/916,886, filed Nov. 1, 2010, entitled SINGLE & MULTI-TRACE OMNIDIRECTIONAL SONDE & LINE LOCATORS AND TRANSMITTERS USED THEREWITH. The content of each of these applications is incorporated by reference herein in its entirety.

Platform embodiment 1200 may further include elements such as a capstan or ratcheting mechanism (not shown), such as the configuration described previously with respect to embodiment 100, to control tightening of the electronic computing system to the platform. In some embodiments additional components such as brackets or clamps to attached tools or other pipe inspection component to the tube frame. In some embodiments, the tube frame or other structural elements may include conductive feet or other conductive elements to provide an electrical connection between electrical components of the system and the ground or other grounded surface.

Figure 13:
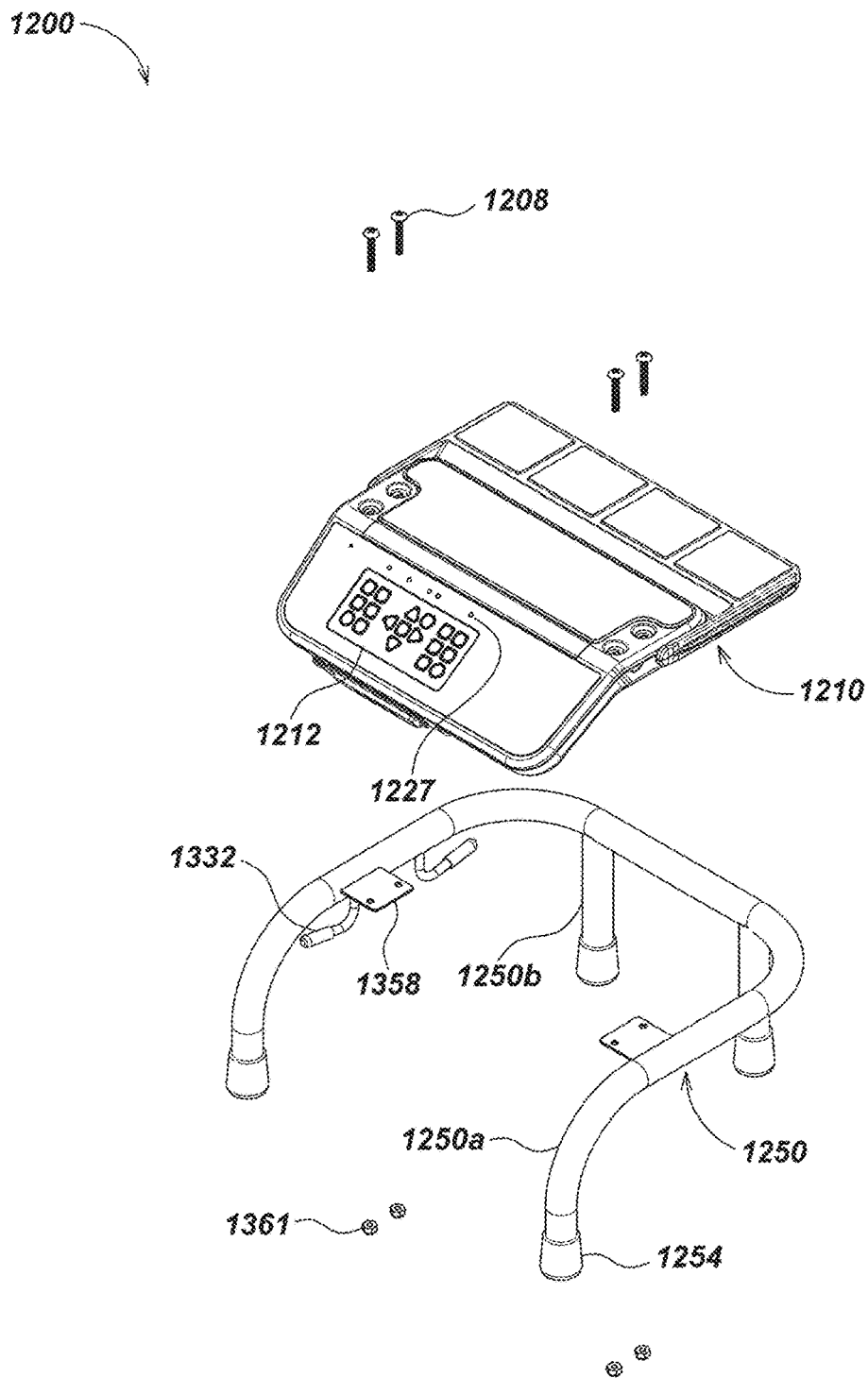
FIG. 13 is an exploded view of the platform embodiment of FIG. 12.

FIG. 13 is an exploded view of the platform embodiment 1200 (FIG. 12) illustrating additional details. In one aspect, frame 1250 may include one or more cord wraps, such as a pair of cord wraps 1332, which may be disposed on the same side of frame 1250, and one or more retaining plates, such as a pair of retaining plates 1358, which may be disposed symmetrically, for example, one on each side of frame 1250. In one aspect, platform 1210 may be mounted to a pair of retaining plates 1358 on frame 1250, with one or more fasteners, such as screws 1208 and nuts 1361.

Figure 14:
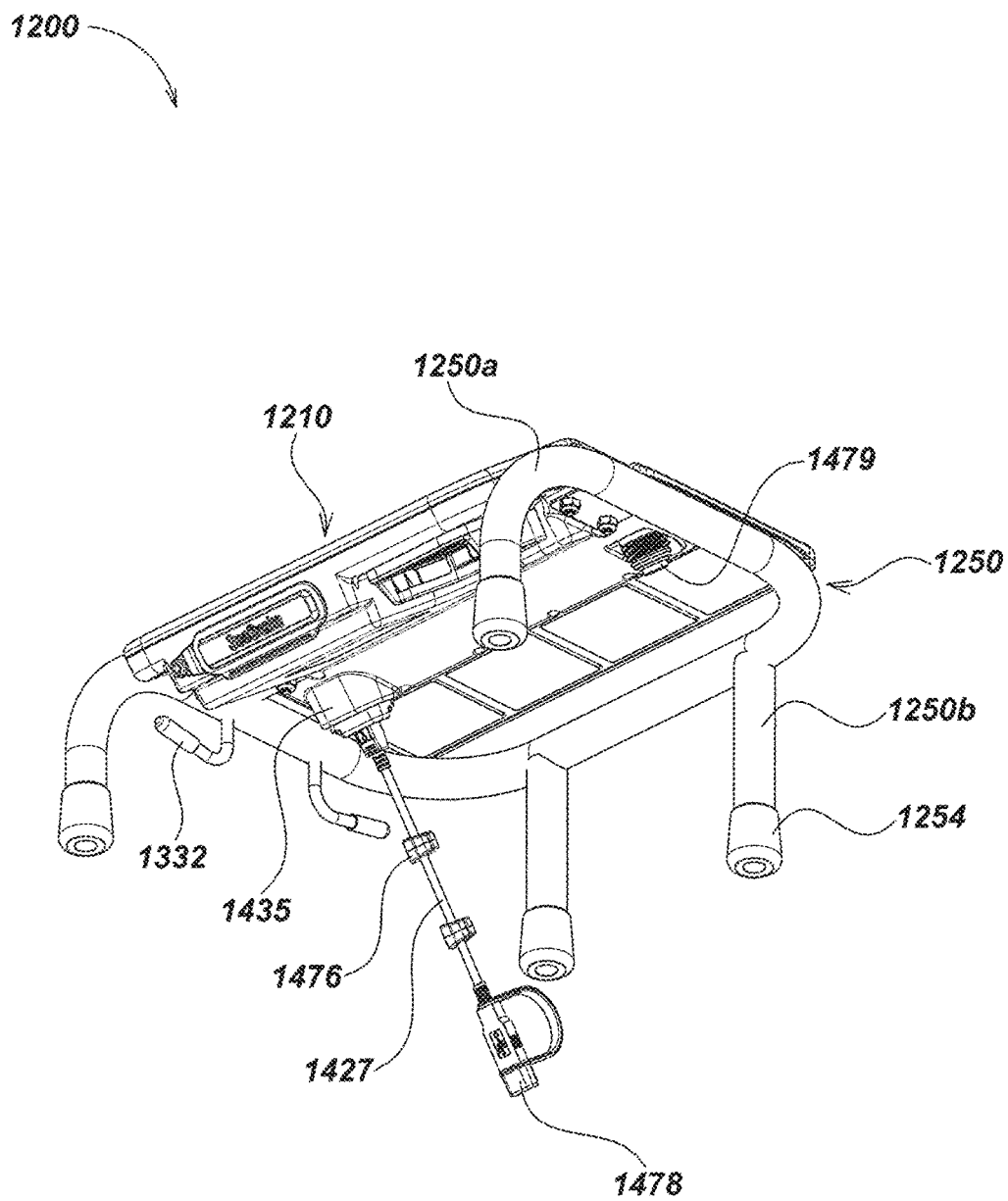
FIG. 14 illustrates details of the platform embodiment of FIG. 12, taken from the underside thereof.

FIG. 14 illustrates additional details of the platform embodiment 1200, shown from the underside thereof. For example, a USB cord 1427 may be electrically connected to the platform 1200 via an interface bus port, such as USB port 1435. A pair of rubber cord clips 1476 may be disposed along the length of USB cord 1427, and a protective dust cap 1478 may be disposed at the end of USB cord 1427. The platform module 1200 may be electrically connected to a pipe inspection cable reel via, for example, a system connection plug 1479, which may be connected to a system cable 226.

Figure 15:
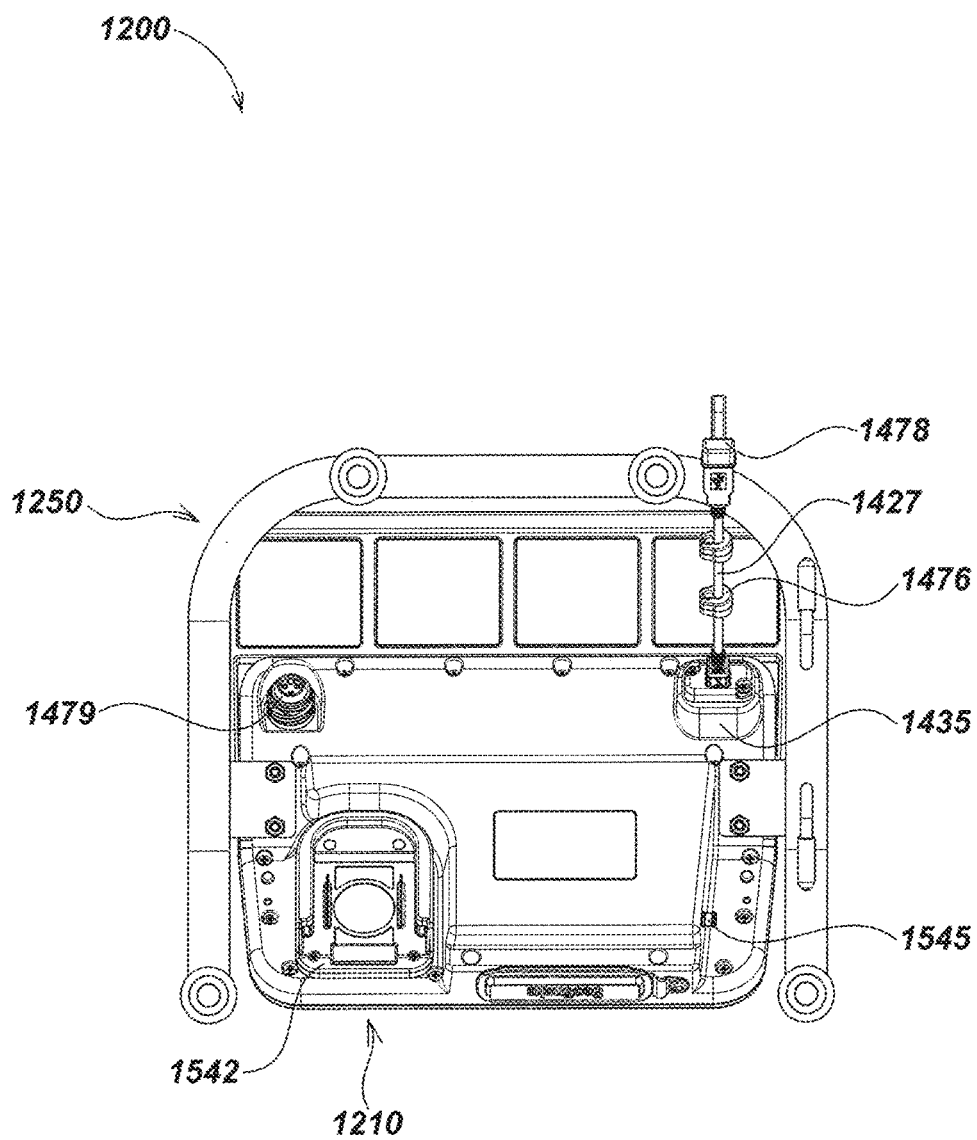
FIG. 15 is a bottom perspective view of the platform embodiment of FIG. 12.

FIG. 15 is a bottom perspective view illustrating addition details of the platform embodiment 1200. For example, a battery shoe 1542 may be disposed on the bottom surface of the platform 1210 for receiving a battery, such an 18V Li-Ion or Li-poly battery pack (not shown in FIG. 15). The battery shoe 1542 and battery pack (not shown in FIG. 15) may be constructed in a manner such as those described in U.S. Patent Application Ser. No. 61/501,172, filed Jun. 24, 2011, and U.S. Patent Application Ser. No. 61/521,262, filed Aug. 8, 2011. The content of each of these applications is incorporated by reference herein in its entirety.

Still referring to FIG. 15, a transmitter clip-on terminal 1545 may be disposed on the underside of platform 1210 for direct connection to a grounded transmitter system (not shown in FIG. 15). For example, a connector, such as an alligator clip disposed at the end of a cord extended from a transmitter (not shown in FIG. 15) may be attached or clipped onto the terminal 1545. Such a platform configuration which may be used for line-tracing a pushrod (not shown in FIG. 15).

Figure 16:
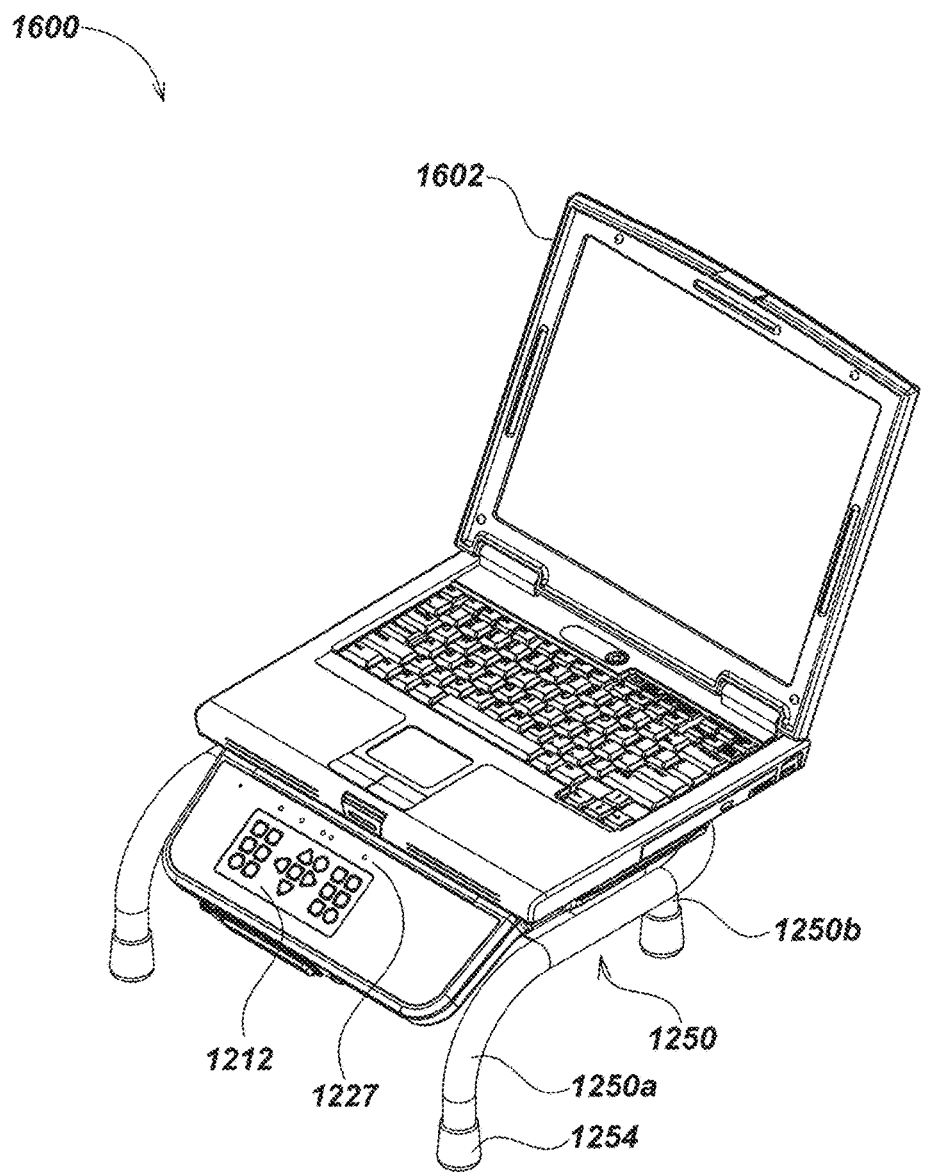
FIG. 16 is an isometric view of an embodiment of a portable camera controller platform of FIG. 12, configured with a display device.

FIG. 16 illustrates details of an embodiment 1600 of a mini camera controller platform such as platform 1200 with a coupled electronic computing device, in this example in the form or a notebook or laptop computer 1602, where the computer's monitor may be used as a display during pipe inspection operations, such providing video or images from a camera head inserted into the pipe or other cavity.

Figure 17:
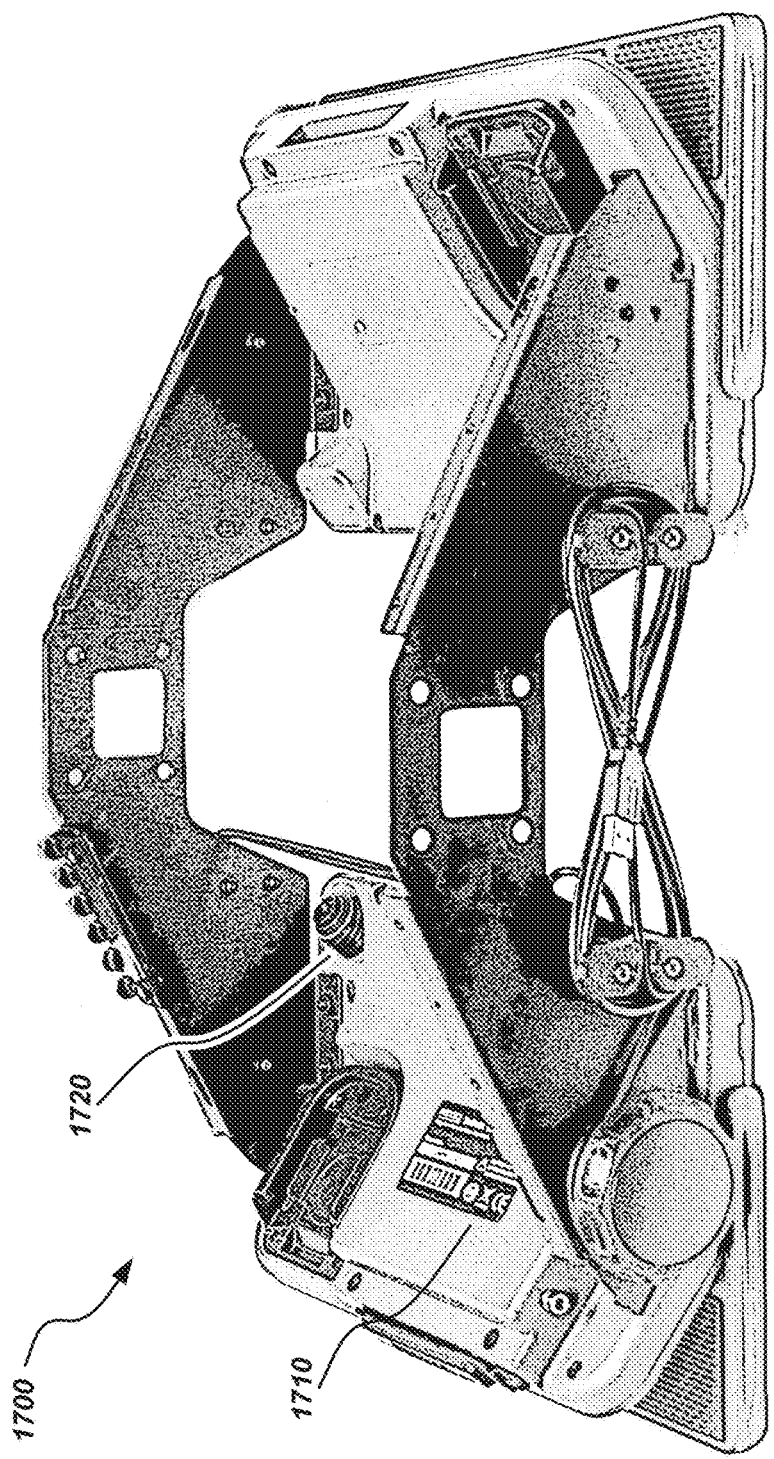
FIG. 17 illustrates additional details of an embodiment of a camera controller platform.

FIG. 17 illustrates details of an embodiment 1700 of a camera controller platform which may correspond with the camera control platforms described previously herein. As shown in FIG. 17, platform 1700 may include a system cable connector or plug 1720, which may correspond with connector 179 as described previously herein. System cable connector 1720 may be used to provide a connection point to a system cable for interconnecting the platform 1700 with other components of a pipe inspection system, such as a cable drum and/or related components (not shown in FIG. 17). An electronics module 1710 (enclosed within the case shown in FIG. 17), which may correspond with the electronics modules described previously herein, may be incorporated on or within a case of the platform to provide the signal processing and other related functions as described herein.

Figure 18:
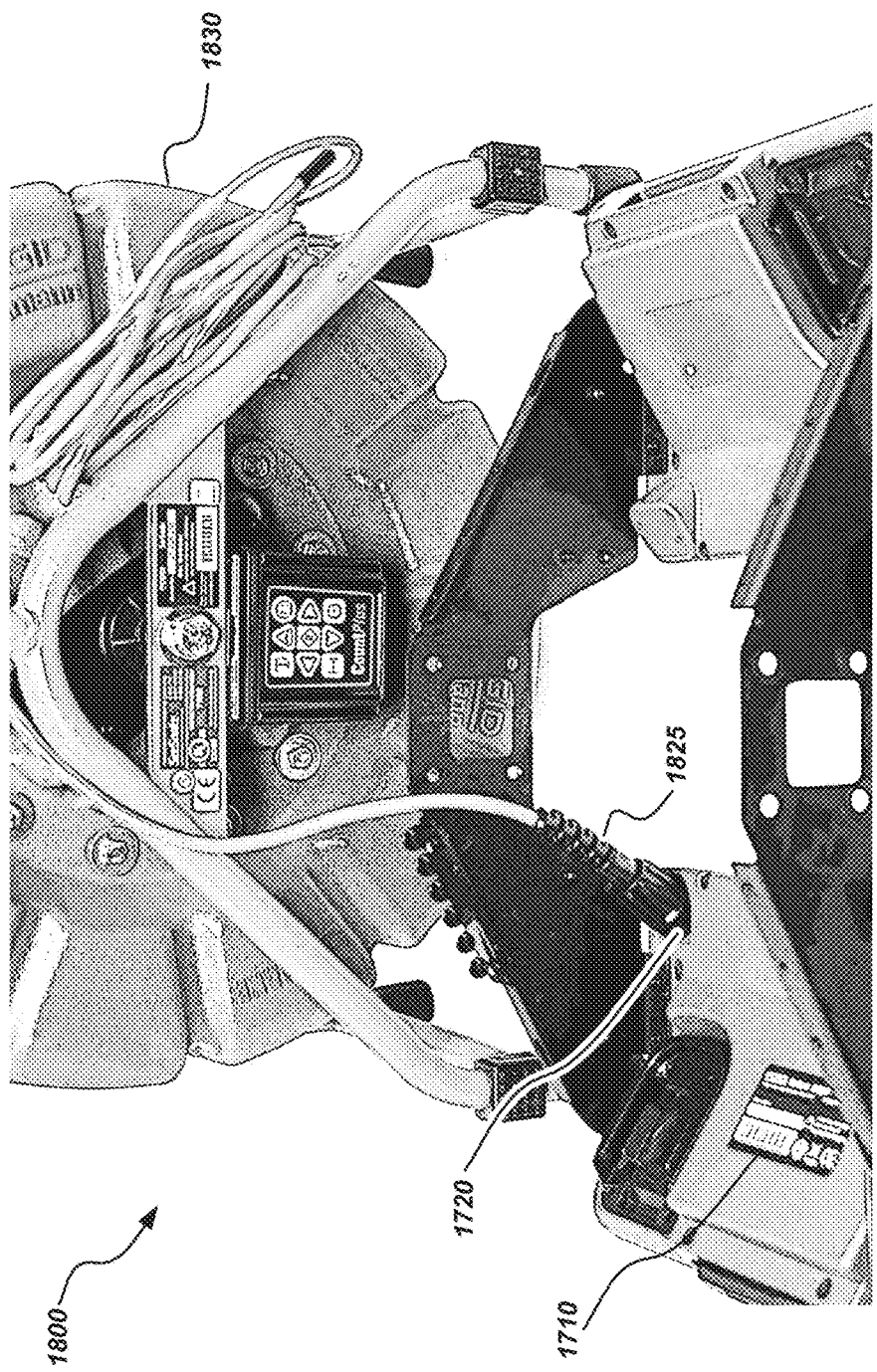
FIG. 18 illustrates additional details of the camera controller platform embodiment of FIG. 17.

FIG. 18 illustrates details of a pipe inspection system embodiment 1800 including platform embodiment 1700 as shown in FIG. 17, along with a cable reel assembly 1830 that may be coupled to the platform 1700 using a system cable 1825 as shown, which may be connected to the platform at system cable connector 1720.

In some embodiments of camera controller platforms, wireless connections between the platform and other pipe inspection system components such as the cable reel drum assembly, sondes or associated transmitters, or other components may be used. These connections may be implemented in place of, or in addition to USB or other wired bus connections. For example, in some embodiments, the USB connection may be replaced with a WI-FI or Bluetooth wireless connection, or other wireless connection such as wireless HDMI, etc., which may be implemented with wireless communication circuits or modules included in or coupled to the electronics module of the camera controller platform. Corresponding wireless circuits or modules may be incorporated in the cable drum assembly, such as in associated electronics components.

In some embodiments, video compression and/or decompression may be implemented to reduce the required bandwidth between various communications connections as described previously. For example, video and/or images may be compressed between the cable drum reel assembly and the camera controller platform electronics module and/or between the camera controller platform electronics module and the electronic computing device (e.g., a notebook, laptop, tablet, smart phone, or other computer or other display or computing device), and/or between other systems. Video may be compressed by techniques known or developed in the art such as, for example, H.264, mJPEG, FLASH, wavelet compression, and the like prior to transmitting to the separate electronic computing or display device. Such a wireless mode of communication may be advantageous in that the electronic computing device/display need not be physically attached to the cable reel drum or other pipe inspection system component.

In some embodiments, all or some of the camera controller platform components, such as, for example, are shown in FIG. 7 and FIG. 8, may be integrated onto or within the cable reel frame or inside the reel. In this configuration, these components would rotate with the reel. In such a configuration, an associated battery may be mounted onto the rotating reel and/or connected electrically using slip rings and mounted on a non-rotating section of the reel/drum assembly.

In some embodiments, a camera controller platform may further include a wireless network base station or hub, such as a WI-FI hub, router, or hot spot to serve a live video feed for viewing in a browser on the electronic computing device or another device within the wireless coverage area. The wireless network base station or hub may be included in or coupled to the electronics module of the camera controller platform and/or may be included on another system component, such as the cable drum assembly. The electronic computing device may, for example, host an HTML5 application to provide enhanced features and device controls. Any WI-FI enabled device may then connect to the pipe inspection system and the live video would be streamed in a browser. In other embodiments, device-specific software application may be used. Additional network-related functions may include, for, example, providing a bridge function, such as via a cellular data connection or other communications link to the "Cloud" to allow a user to upload images (snapshots), video, audio, or other data or information to a central server system or other networked system. Network printing functionality may be included to allow the camera control unit to incorporate a printer and/or connect to a network-enabled printer to provide data or information, e.g., measurement parameters, snapshot images, or other information or data as described herein to a network enabled printer. An "auto log" function may be included to locally store data and information and automatically sync to network storage when the user (e.g., a plumber) returns to an office.

In some embodiments, a camera controller platform may further include a module to provide one-to-many streaming data, such as a streaming router or other streaming-capable device. In this configuration, data, such as video signals, images, audio, or other data or information may be sent to multiple users at the same time. For example, during a home pipe inspection operation, a homeowner may be able to simultaneously view video from within their home or yard while a pipe is being inspected, or information may be provided to multiple users during training or demonstrations. Restrictions on the types of information accessible may be included in such as configuration, such as by providing full information to an administrator or primary user, and limited information to guest users or others.

In video display applications it may be desirable to configure the system to minimize video latency with no buffering. For example, the system may be configured to drop frames rather than buffer data to provide an impression of fast responsiveness to a user. Graphical feedback of motion may be provided when dropping video frames. For example, a fake motion blur, a moving arrow, increasing the count, or other mechanisms may be used to provide feedback to an operator to create an impression of responsiveness.

In some embodiments where a wireless hub or hot-spot (such as, for example, a WI-FI hotspot) is included in a camera controller platform, additional functionality, such as hardware and/or software to implement a configuration menu to create customer SSID's may be included. For example, each camera controller platform may be configured to allow a user to create his or her own SSID (e.g., "Joe Plumber's Camera," etc.).

In some embodiments, the electronic computing device (e.g., notebook or laptop computer, tablet, smart phone, etc.) may be configured to provide additional functionality, such as controlling status and feedback for sondes, lights (e.g., lighting deployed within pipes or other cavities, transmitters, actuators, gas or liquid sensors, additional microphones or other audio or ultrasonic capture devices, and the like. Information such as battery status, memory or storage device (e.g., USB thumb drive, compact flash, SD, or other data storage device) capacity or remaining storage space, component failures or status information, or other parameters may likewise be shared between the electronic computing device and the camera controller platform/electronics module(s).

Clearly, other embodiments and modifications of this disclosure may occur readily to those of ordinary skill in the art in view of these teachings. Therefore, the protection afforded this disclosure is to be limited only by the following claims, which include all such embodiments and modifications when viewed in conjunction with the above specification and accompanying drawing.

In some configurations, the apparatus, circuit, modules, or systems described herein may include means for implementing features or providing functions described herein. In one aspect, the aforementioned means may be a module including a processor or processors, associated memory and/or other electronics in which embodiments of the disclosure reside, such as to implement signal processing, switching, transmission, reception, or other functions to process video or data signal inputs, and/or to provide other electronic functions described herein. These may be, for example, modules or apparatus residing in pipe inspection systems, camera controller platforms, electronics modules, user interface modules, display devices, electronic computing devices, coupling apparatus, and/or other related equipment or devices.

In one or more exemplary embodiments, the electronic functions, methods and processes described herein and associated with pipe inspection systems, camera controller units, electronics modules, electronic computing devices, display devices, coupling apparatus, and pipe inspection system components such as cable reels and related electronics may be implemented in hardware, software, firmware, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

As used herein, computer program products comprising computer-readable media including all forms of computer-readable medium except, to the extent that such media is deemed to be non-statutory, transitory propagating signals.

It is understood that the specific order or hierarchy of steps or stages in the processes and methods disclosed herein are examples of exemplary approaches. Based upon design preferences, it is understood that the specific order or hierarchy of steps in the processes may be rearranged while remaining within the scope of the present disclosure unless noted otherwise.

Those of skill in the art would understand that information and signals, such as video and/or audio signals or data, control signals, or other signals or data may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, electro-mechanical components, or combinations thereof. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein and, for example, in a processing element as described herein may be implemented or performed with a general purpose processor or processors, a digital signal processor (DSP), an application specific integrated circuit (ASIC), a field programmable gate array (FPGA) or other programmable logic device, discrete gate or transistor logic, discrete hardware components, or any combination thereof designed to perform the processing functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. A processing element may furthering include or be coupled to one or more memory elements for storing instructions, data, and/or other information in a digital storage format.

The various illustrative functions and circuits described in connection with the embodiments disclosed herein with respect to camera and lighting elements may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps or stages of a method, process or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known or developed in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The claims are not intended to be limited to the aspects shown herein, but is to be accorded the full scope consistent with the disclosure herein, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

The previous description of the disclosed aspects is provided to enable any person skilled in the art to make or use embodiment of the present invention. Various modifications to these aspects will be readily apparent to those skilled in the art, and the generic principles defined herein may be applied to other aspects without departing from the spirit or scope of the invention. Thus, the present invention is not intended to be limited to the aspects shown herein but is to be accorded the widest scope consistent with the following claims and their equivalents.

The disclosure is not intended to be limited to the aspects shown herein, but is to be accorded the full scope consistent with the specification and drawings, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the spirit or scope of the disclosure. Thus, the disclosure is not intended to be limited to the aspects shown herein but is to be accorded the widest scope consistent with the following claims and their equivalents.

We claim:

1. A camera controller platform, comprising:
a base assembly to mechanically couple to a pipe inspection system, the pipe inspection system including a cable reel drum assembly and a camera head, wherein the base assembly comprises at least two substantially flat platforms having corresponding panels extending angularly downward from outer edges of the substantially flat platforms;
one or more electronic elements integrated into one or more of the substantially flat platforms or corresponding panels, the electronic elements including a user interface panel, disposed on or in one of the panels of the base assembly, to provide control input signals to the camera head;
a capstan assembly including a flexible tensioning element to mechanically couple an electronic computing device to the top of the base assembly above the user interface panel;
at least two wings coupled to the substantially flat platforms such that the wings are retractable from the substantially flat platforms to an extended position abutting against one another to cooperatively form, in conjunction with the substantially flat platforms, an extended working surface on the base assembly, the wings are further rotatable outwardly from a top center area of the base assembly; and
an electronics module coupled to the one or more electronic elements including the user interface panel, the electronics module including one or more processing elements including instructions to cause a processor to:
receive the control input signals from the user interface panel and provide control data to the pipe inspection system; and
receive one or more pipe inspection output signals from the pipe inspection system and provide data corresponding to the pipe inspection output signals to the coupled electronic computing device.

2. The platform of claim 1, wherein one or more of the wings are folding wings.

3. The platform of claim 1, wherein one or more of the wings are retractable into the base assembly.

4. The platform of claim 1, further including a Universal Serial Bus (USB) hub coupled to the electronics module.

5. The platform of claim 1, further including a connector coupled to the electronics module for receiving signals from a system cable connected to the from pipe inspection system.

6. The platform of claim 1, further including a wireless communication module coupled to the electronics module for receiving wirelessly communicated signals from the pipe inspection system.

7. The platform of claim 1, further including a hub or router configured to wirelessly provide information from the pipe inspection system.

8. The platform of claim 7, wherein the information provided from the hub or router includes images or video signals.

9. The platform of claim 1, further including a capstan assembly and a tensioning element configured to secure an electronic computing device to the platform.

10. The platform of claim 9, wherein the capstan assembly is configured to limit the torque applied to the electronic computing device when secured to the platform.

11. The platform of claim 10, wherein the capstan assembly includes tooth and spring elements to limit the applied torque.

12. The platform of claim 1, wherein the pipe inspection output signals are video signals and the video signals are converted to digital signals in accordance with an interface bus standard.

13. The platform of claim 12, wherein the interface bus is a Universal Serial Bus (USB).

14. The platform of claim 1, further including a microphone, wherein the electronics module is further configured to receive an audio signal from the microphone and associate the audio signal with the digital signals.

15. The platform of claim 1, wherein the output signals from the pipe inspection system are video signals and the video signals are compressed before being provided to the electronic computing system.

16. A pipe inspection system, comprising:
a cable reel drum assembly;
a push-cable coupled to the cable-reel drum assembly;
a camera head coupled to a distal end of the push-cable;
an interface circuit configured to electronically couple the camera head to a first end of a system cable; and
a camera controller platform including:
a base assembly to mechanically couple to to the cable reel drum assembly, the base assembly comprising at least two substantially flat platforms having corresponding panels extending angularly downward from outer edges of the substantially flat platforms;
a plurality of electronic elements integrated into one or more of the substantially flat platforms or corresponding panels, the electronic elements including a user interface panel, disposed on or in one of the panels of the base assembly, to provide control input signals to the camera head, and a wireless communication module;
an electronic computing device including a display screen, wirelessly coupled to the base assembly through the wireless communication module;
one or more rotating wings coupled to the base assembly to rotate outward from the top center area of the base assembly; and
an electronics module coupled to the electronic elements, the electronics module including one or more processing elements configured to:
receive the control input signals from the user interface panel and provide control data to the pipe inspection system; and
receive one or more pipe inspection output signals from the pipe inspection system and provide data corresponding to the pipe inspection output signals to the wirelessly coupled electronic computing device; and
a system connector coupled to the electronics module and to a second end of the system cable.

17. The system of claim 16, wherein the platform is incorporated at least in part into the cable reel drum assembly.

18. A camera controller platform with integrated camera control unit (CCU) elements, for mechanically coupling to a pipe inspection system including a cable reel drum assembly and a camera head, the camera controller platform comprising:
a base assembly to mechanically couple to the cable reel drum assembly, the base assembly comprising at least two substantially flat platforms having corresponding panels extending from outer edges of the substantially flat platforms;
at least two wings coupled to the substantially flat platforms such that the wings are retractable from the substantially flat platforms to an extended position abutting against one another to cooperatively form, in conjunction with the substantially flat platforms, a substantially continuous and extended working surface on the base assembly, the wings are further rotatable outwardly from a top center area of the base assembly;
an electronic computing device including a display screen, mechanically or wirelessly coupled to the base assembly; and
a plurality of integrated camera control unit elements disposed in or on one or more of the substantially flat platforms or corresponding panels of the base assembly, the integrated camera control unit elements including:
a user interface panel, disposed on one of the panels of the base assembly, to provide control input signals for controlling operation of the camera head; and
an electronics module coupled to the user interface panel, the electronics module including one or more processing elements to:
receive the control input signals from the user interface panel and provide the received control input signals to the camera head; and
receive one or more camera output signals from the camera head, and provide data corresponding to the camera output signals for display onto the display screen of the coupled electronic computing device.

* * * * *